(12) United States Patent
Karchmer et al.

(10) Patent No.: US 10,467,382 B2
(45) Date of Patent: Nov. 5, 2019

(54) CONCEIVABLE BASAL BODY TEMPERATURES AND MENSTRUAL CYCLE

(71) Applicant: Conceivable, Inc., Austin, TX (US)

(72) Inventors: Kirsten Karchmer, Austin, TX (US); Witold Krassowski, Austin, TX (US); Jonathan Berkowitz, Austin, TX (US)

(73) Assignee: Brazen Incorporated, Austin, TX (US)

( * ) Notice: Subject to any disclaimer, the term of this patent is extended or adjusted under 35 U.S.C. 154(b) by 853 days.

(21) Appl. No.: 14/541,553

(22) Filed: Nov. 14, 2014

(65) Prior Publication Data

US 2016/0140314 A1    May 19, 2016

(51) Int. Cl.
| | | |
|---|---|---|
| G06F 19/00 | (2018.01) | |
| A61B 5/00 | (2006.01) | |
| G09B 19/00 | (2006.01) | |
| A61B 5/01 | (2006.01) | |
| A61B 10/00 | (2006.01) | |

(52) U.S. Cl.
CPC ............ *G06F 19/3456* (2013.01); *A61B 5/01* (2013.01); *A61B 5/4306* (2013.01); *A61B 10/0012* (2013.01); *G09B 19/00* (2013.01); *A61B 2010/0019* (2013.01)

(58) Field of Classification Search
CPC ... G06F 19/3456; G09B 19/00; A61B 5/4306; A61B 5/01; A61B 10/0012; A61B 2010/0019
USPC ............................ 600/33–35; 434/236; 705/2
See application file for complete search history.

(56) References Cited

U.S. PATENT DOCUMENTS

| | | | | |
|---|---|---|---|---|
| 4,006,227 A * | 2/1977 | Gallegos | ................. | A61K 36/28 424/764 |
| 6,610,331 B1 * | 8/2003 | Sweazy | ................... | A61K 45/06 424/725 |
| 8,834,389 B2 * | 9/2014 | Schafer | .............. | A61B 10/0012 600/551 |
| 2005/0143359 A1 * | 6/2005 | Bell | ........................ | A61K 31/56 514/170 |
| 2008/0102141 A1 * | 5/2008 | Brandes | ................. | A61K 36/28 424/728 |
| 2008/0162352 A1 * | 7/2008 | Gizewski | ............ | G06F 19/3456 705/50 |
| 2009/0163454 A1 * | 6/2009 | Hait | ..................... | A61K 31/565 514/170 |
| 2009/0234200 A1 * | 9/2009 | Husheer | ............... | A61B 5/0008 600/301 |
| 2010/0280838 A1 * | 11/2010 | Bosworth | .............. | G06Q 50/22 705/2 |
| 2011/0184247 A1 * | 7/2011 | Contant | ................. | G06Q 10/10 600/300 |
| 2013/0054150 A1 * | 2/2013 | Sacks | ................. | A61B 10/0012 702/19 |

(Continued)

*Primary Examiner* — Navin Natnithithadha
*Assistant Examiner* — Sunita Reddy
(74) *Attorney, Agent, or Firm* — DLA Piper LLP (US)

(57) ABSTRACT

The present invention discloses software programs, systems and methods for increasing the chances of users conception by maximizing the user's fertility potential by providing a software program that combines identifying the underlying causes of infertility and using best practices as described by current medical literature for fertility changes along with herbal recommendations to provide personalized wellness recommendations that give the individual user the power to improve their natural fertility.

7 Claims, 28 Drawing Sheets

(56) References Cited

U.S. PATENT DOCUMENTS

| | | | | |
|---|---|---|---|---|
| 2013/0338123 | A1* | 12/2013 | Bernick | A61K 31/57 514/170 |
| 2014/0094421 | A1* | 4/2014 | Sepahvand | A61K 31/7034 514/25 |
| 2014/0155492 | A1* | 6/2014 | Bendera | A61K 31/132 514/674 |
| 2014/0249379 | A1* | 9/2014 | Proud | A61B 5/0015 600/301 |
| 2015/0031775 | A1* | 1/2015 | Bendera | A61K 31/132 514/674 |
| 2016/0213354 | A1* | 7/2016 | Levin | A61B 5/7275 |
| 2017/0071581 | A1* | 3/2017 | Sacks | A61B 10/0012 |

\* cited by examiner

FIG. 7

| Total Score | Cycle Health | BBT | Profile | Lifestyle |
|---|---|---|---|---|
| 100 | 30 | 40 | 10 | 20 |

FIG. 11A

| Total Score | Length | Days Bleeding | Color | Clotting | Volume | Cramping | PMS | Cervical Fluid |
|---|---|---|---|---|---|---|---|---|
| 100 | 20 | 15 | 10 | 10 | 15 | 10 | 10 | 10 |
| Scoring | 28 = 20 | 0 = P? | Fresh = 10 | | Soaks a pad in: | Scale of 1-10 | Severity 1-5 | |
| | Dev of 1 = 18 | 1 = 0 | Pale = 6 | None = 10 | <2 = 0 | 0 = 10 | 0 = 5 | Copious = 3 |
| | 2 = 14 | 2 = 3 | Rusty = 6 | Then per incidence | 2 = 6 | 1 = 8 | 1 = 4 | Clear = 3 |
| | 3 = 8 | 3 = 9 | Brown = 4 | dime = -1 | 4 = 15 | 2 = 6 | 2 = 3 | Sticky = 3 |
| | 4 = 2 | 4 = 15 | Blue = 0 | quarter = -2 | 6 = 8 | 3 = 4 | 4 = 1 | Plus 1 for all 3 |
| | 5+ = 0 | 5 = 12 | Black = 0 | half doller = -4 | 8 = 4 | 4 = 2 | 5 = 0 | |
| | | 6 = 9 | | | 10 = 2 | 5 = 0 | Symptoms | |
| | | 7 = 3 | | | 12+ = 0 | | -1 for each symptom | |
| | | 8+ = 0 | | | | | | |

FIG. 11B

| Total Score | Volatility | | Avrg Fol Temp | | Avrg Lut Temp | | Fol Length | | Lut Length | |
|---|---|---|---|---|---|---|---|---|---|---|
| 100 | | 20 | | 20 | | 20 | | 20 | | 20 |
| Scoring | SD =.1 = 20 | | 97.2-4 = 20 | | 98.2+ = 20 | | 6 = 0 | | 15+ = 20 | |
| | .15 = 16 | | 97.4-6 = 15 | | 98.0-2 = 15 | | 7 = 5 | | 14 = 20 | |
| | .2 = 12 | | 97.6-8 = 10 | | 97.8-98.0 = 10 | | 8 = 10 | | 13 = 15 | |
| | .25 = 6 | | 97.8-98.0 = 5 | | 97.6-8 = 5 | | 9 = 15 | | 12 = 10 | |
| | >.3 = 0 | | 98+ = 0 | | <97.6 = 0 | | 10 = 20 | | 11 = 5 | |
| | | | 97.0-2 = 15 | | | | 11 = 18 | | <10 = 0 | |
| | | | 96.8-97.0 = 10 | | | | 12 = 16 | | | |
| | | | 96.6-8 = 5 | | | | 13 = 12 | | | |
| | | | <96.6 = 0 | | | | 14 = 8 | | | |
| | | | | | | | 15 = 4 | | | |
| | | | | | | | 16+ = 0 | | | |

FIG. 11C

| Total Score | Hot | Cold | Stuck | Pale | Tired | Energy | Digestion | Elimination | Sleep Qual | Mood |
|---|---|---|---|---|---|---|---|---|---|---|
| 100 | 15 | 15 | 15 | 15 | 15 | 5 | 5 | 5 | 5 | 5 |
| Scoring | 5=0 | 5=0 | 5=0 | 5=0 | 5=0 | Rank 1-5 | 5 for normal | 5 for normal | 5 for normal | 5 if happy |
| | 4=3 | 4=3 | 4=3 | 4=3 | 4=3 | | 0 for other | 0 for other | 0 for other | 0 for other |
| | 2=9 | 2=9 | 2=9 | 2=9 | 3=6 | | | | | |
| | 1=12 | 1=12 | 1=12 | 1=12 | 2=9 | | | | | |
| | 0=15 | 0=15 | 0=15 | 0=15 | 1=12 | | | | | |
| | | | | | 0=15 | | | | | |

FIG. 11D

| Total Score | Herbs | Sleep | Hydration | Diet |
|---|---|---|---|---|
| 100 | 40 | 30 | 15 | 15 |
| Scoring | Miss 1 dose in a day= -1 | 8+=30 | 8+=15 | 8+=15 |
| | Miss 2 dose in a day= -3 | 7=25 | 7=13 | 7=13 |
| | Miss 3 dose in a day= -5 | 6=20 | 6=11 | 6=11 |
| | | 5=15 | 5=9 | 5=9 |
| | | 4=10 | 4=7 | 4=7 |
| | | <3=0 | 3=5 | 3=5 |
| | | | 2=3 | 2=3 |
| | | | 1=0 | 1=0 |

FIG. 11E

| recommen-dation_id | title | body |
|---|---|---|
| 1 | Clotting | During your menstrual cycle, incorporate more foods that help improve circulation like oranges, ginger, dark chocolate, and salmon. Cold causes the capillaries to constrict and reduces blood circulation. Stay warm when you menstruate and save the low rise jeans and flip flops for later in the month. |
| 2 | Clotting | Oh no, my cycle got worse!! Try not to worry, sometimes, as your cycle adjusts, it will fluctuate. Stay on track with your program and your body will respond to your hard work. |
| 3 | Clotting | Way to go! Your hard work is showing up in your menstrual cycle! You have improved from last cycle. |
| 4 | Cramping | The warming effects of ginger can help relieve mild menstrual pain symptoms. Brew a tea with hot water and a few slices of fresh ginger for 5 min. A touch of honey sweetens the pot! |
| 5 | Cramping | It may seem obvious but a heating pad can do wonders for moderate menstrual cramps. |
| 6 | Cramping | It may seem obvious but a heating pad can do wonders for moderate menstrual cramps. |
| 7 | Cramping | Really hurting? Try sitting on your knees ( if you can ) and lean back as far as you can. Try to rest like this for 3 min breathing deeply into your abdomen. |
| 8 | Cramping | Really hurting? Try sitting on your knees ( if you can ) and lean back as far as you can. Try to rest like this for 3 min breathing deeply into your abdomen. |
| 9 | Cramping | Ouch, your pain is worse this cycle. Keep your head up. As your cycle begins to regulate, it may get a little worse before it gets better. Be sure to rank your stuck hurdle high this month so Conceivable knows to work harder for you in this area for next month. |
| 10 | Cramping | Improvement in menstrual pain is a good indicator that your body is doing a better job of building and shedding a healthy uterine lining each cycle. Sounds like you're getting the luxury suite ready for baby! |
| 11 | Volume | Unless there are a lot of clots in your blood, you might benefit from a lower dose of Release. |
| 12 | Volume | In order to make a fantastic, lush lining, you need to make some more blood, sister. Try increasing iron rich foods like, greens, lentils, raspberries, blueberries, and dried apricots, |

1201 → rows 1–3
1202 → rows 4–10
1203 → rows 11–12

FIG. 12A

|   |   |   |
|---|---|---|
| 1203 { | 13 | Volume | Keep eating lots of iron rich foods! |
|   | 14 | Color | If your blood is pale red, you would probably benefit from really pumping up the iron rich foods. Eat a bit more red meat, wild salmon, and dark berries. |
|   | 15 | Color | Yippee, you are getting more fertile every month. Keep up the great work. Your body thanks you. |
| 1204 { | 16 | Color | Rank your Hot hurdle a little higher next month and eat more cooling foods during cycle days 4-14 like, cucumber, hibiscus tea, and mint. |
|   | 17 | Color | Rank your Hot hurdle a little higher next month and eat more cooling foods during cycle days 4-14 like, cucumber, hibiscus tea, and mint. |
|   | 18 | Color | Be sure to check with your dr. to make sure your thyroid is functioning properly and stay as warm as possible. Wool socks really do make a difference. |
|   | 19 | Color | Try to limit the foods that make stuck conditions worse like caffeine, greasy foods, heavy and complex meals. |
| 1205 { | 20 | Ovulation | Be sure to take your herbs and incorporate a bit more raw food into your diet, including superfoods like spirulina. |
| 1206 { | 21 | Cervical Fluid | The presence of fertile cervical fluid means it's baby making time, go get busy! |
|   | 22 | Cervical Fluid | Be sure to take your herbs and incorporate a bit more raw food into your diet, including superfoods like spirulina. |
| 1207 { | 23 | PMS Severity | How to unstick stuck? Try to manage your stress more carefully during this phase. Be sure to avoid caffeine, alcohol and greasy foods. Regular moderate exercise (even a 20 min walk at lunch) goes a very long way! |
| 1208 { | 24 | PMS Symptoms | Gentle breast massage can do wonders to relieve your symptoms while you are getting unstuck. See how here! |

FIG. 12A (Cont.)

| | | |
|---|---|---|
| 25 | PMS Symptoms | Make work a little easier for your digestion in the weeks prior to your period. Try to eat simply, with fewer heavy and difficult to digest foods. Sour foods like lemon apple cider vinegar may help regulate liver and hormone function. |
| 26 | PMS Symptoms | When you are feeling moody, try taking a tablespoon of apple cider vinegar with a glass of water and watch your mood improve pretty quickly |
| 27 | PMS Symptoms | PMS is the personification of being stuck. Pay close attention to how your pms presents because it can tell you so much about how your body is functioning! |
| 28 | PMS Symptoms | Headaches related to PMS require a delicate balance of rest and invigoration. After ovulation, try to get some extra minutes of sleep and sleep in on the weekends. Balance that with some regular mild to moderate exercise. Even a 20min walk at lunch will help! |
| 29 | Spotting | The good news is that you will notice the bleeding getting more regular as you unstick! Keep taking your herbs. |
| 30 | Follicular Temperature | Pay attention to eating the highest quality foods you can get your hands on, rest a ton and stay warm! |
| 31 | Follicular Temperature | Let's keep it cool this month. Stay hydrated, try cucumber water, and chamomile tea, and focus on eating cooling foods. You can find a list here. [link to cooling food list] |
| 32 | Follicular Temperature | This month try incorporating some frustration alleviating tactics like singing in your car, getting a bit more exercise, or trying some breathing exercises. |
| 33 | Luteal Temperature | The easiest thing is to stay warm. Add more warming foods to your diet like cinnamon, ginger, lamb and onions/garlic. |
| 34 | Luteal Temperature | This month try incorporating some frustration alleviating tactics like singing in your car, getting a bit more exercise, or trying some breathing exercises. |
| 35 | Luteal Temperature | You're able to sustain enough energy to keep your luteal BBT's elevated for a few days, but then peter out for the rest of the cycle. Focus on getting more rest, taking naps, and eating as well as possible! |

Rows 25–28: 1208
Row 29: 1209
Rows 30–32: 1210
Rows 33–35: 1211

FIG. 12B

| | | |
|---|---|---|
| 36 | Sleep | Sleep is so essential to your health and well being. What's one small thing you can do to improve your week? If you're a chronic non-sleeper, you might try taking 5mg of melatonin at bed. |
| 37 | Sleep | Stimulating your brain with bright light before bed can lead to disrupted sleep - just for tonight, try going without screens (computer, tv, phone) for the hour before you hop in bed. |
| 38 | Sleep | A little more sleep can go a long way. Try going to bed 15 minutes earlier tonight. |
| 39 | Sleep | Let's get friendly with that snooze button. Shut those eyes a little longer each night for vibrant skin, more energy, better mood, and increased menstrual regularity. |
| 40 | Sleep | Let's get friendly with that snooze button. Shut those eyes a little longer each night for vibrant skin, more energy, better mood, and increased menstrual regularity. |
| 41 | Sleep | |
| 42 | Water | Even big changes start with little steps. Can you drink just one more glass of water today? |
| 43 | Water | You're halfway to ideal hydration. Treat yourself to a glass or warm water with lemon when you wake up tomorrow morning! |
| 44 | Water | You're halfway to ideal hydration. Treat yourself to a glass or warm water with lemon when you wake up tomorrow morning! |
| 45 | Water | Mix up your water routine so you don't get bored - add sliced cucumber, mint, strawberries, lemon, or chamomile to sparkling water for a refreshing treat. |

FIG. 12B (Cont.)

| | | |
|---|---|---|
| 46 | Water | Mix up your water routine so you don't get bored - add sliced cucumber, mint, strawberries, lemon, or chamomile to sparkling water for a refreshing treat. |
| 47 | Water | |
| 48 | Veggies | Getting more veggies in your diet starts with getting them to your house. Next time you're at the grocery store, shop on the outside (fresh produce, butcher, seafood, etc....) and stay out of the aisles. |
| 49 | Veggies | Need help getting more veggies in your diet? Always serve the veggies first and make sure that half your plate gets filled with veggies before anything else goes on. |
| 50 | Veggies | Need help getting more veggies in your diet? Always serve the veggies first and make sure that half your plate gets filled with veggies before anything else goes on. |
| 51 | Veggies | Start your day with a veggie boost. Green smoothies and fresh squeezed juices are a great way to sneak in a couple extra servings of veggies every day. |
| 52 | Veggies | Start your day with a veggie boost. Green smoothies and fresh squeezed juices are a great way to sneak in a couple extra servings of veggies every day. |
| 53 | Veggies | |
| 54 | Energy | Low energy is one of the biggest indicators that the Tired hurdle is still in your way. Usually it's also an indicator that something is lacking in diet, hydration, or sleep. Pay particular attention to where your lifestyle scores are lowest and get to work! |
| 55 | Energy | Low energy is one of the biggest indicators that the Tired hurdle is still in your way. Usually it's also an indicator that something is lacking in diet, hydration, or sleep. Pay particular attention to where your lifestyle scores are lowest and get to work! |

Rows 46–47 grouped as 1213; rows 48–53 grouped as 1214; rows 54–55 grouped as 1215.

FIG. 12C

| | | |
|---|---|---|
| 1215 { | 56 Energy | To be your most Conceivable self, we need you brimming with energy. After all, baby making is a lot of work! It sounds like you're struggling with the Tired hurdle. Pay attention to sleep, diet, and hydration and things should slowly improve! |
| | 57 Energy | To be your most Conceivable self, we need you brimming with energy. After all, baby making is a lot of work! It sounds like you're struggling with the Tired hurdle. Pay attention to sleep, diet, and hydration and things should slowly improve! |
| | 58 Energy | Keep your energy levels high by getting good rest and eating nutrient rich foods. |
| 1216 { | 59 Stress | Serenity is not freedom from the storm, it is peace within it. Find time today to take 5 deep breaths, and think of one thing that can make your life more peaceful. |
| | 60 Stress | Serenity is not freedom from the storm, it is peace within it. Find time today to take 5 deep breaths, and think of one thing that can make your life more peaceful. |
| | 61 Stress | Move more! When your body's stagnant, your mood gets stagnant too. Try going for a walk, taking a yoga class, getting a massage, anything that engages your body and soothes the mind. |
| | 62 Stress | Move more! When your body's stagnant, your mood gets stagnant too. Try going for a walk, taking a yoga class, getting a massage, anything that engages your body and soothes the mind. |
| | 63 Stress | |
| 1217 { | 64 Digestion | Congee (the Chinese version of oatmeal) is a great way to boost your metabolism and heal your digestive system. Try it for breakfast this week! |
| | 65 Digestion | Congee (the Chinese version of oatmeal) is a great way to boost your metabolism and heal your digestive system. Try it for breakfast this week! |

FIG. 12C (Cont.)

| | | |
|---|---|---|
| 66 | Digestion | Congee (the Chinese version of oatmeal) is a great way to boost your metabolism and heal your digestive system. Try it for breakfast this week! |
| 67 | Digestion | Try mixing a tablespoon of apple cider vinegar with a small glass of water to treat occassional heartburn. |
| 68 | Digestion | A glass of chamomile or ginger tea can calm an angry tummy. Also make sure you avoid common irritants like coffee, alcohol, and spicy foods. |
| 69 | Digestion | |
| 70 | Sleep Quality | Avoid caffeinated beverages or eating food too close to going to sleep. Asking you body to process these things while you are sleeping will cause disruptions to your sleep. |
| 71 | Sleep Quality | Avoid using your phone or bright screen activley in bed before you go to sleep. |
| 72 | Sleep Quality | |
| 73 | Mood | Move more! When your body's stagnant, your mood gets stagnant too. Try going for a walk, taking a yoga class, getting a massage, anything that engages your body and soothes the mind. |

Rows 66–69 grouped as 1217; rows 70–72 grouped as 1218; row 73 as 1219.

FIG. 12D

| | | |
|---|---|---|
| 74 | Mood | Fear is a natural emotion, and one that's perfectly acceptable to feel! By identifying our fears we can create strategies to navigate them. What's one thing you're afraid of? How can that fear motivate you to make positive changes in your life? |
| 75 | Mood | |
| 76 | Mood | Move more! When your body's stagnant, your mood gets stagnant too. Try going for a walk, taking a yoga class, getting a massage, anything that engages your body and soothes the mind. |
| 77 | Mood | We can learn to silence the mind, but it takes practice. That's what meditation is all about. Start by closing your eyes and focusing on the breath. Count your breaths on the exhale up to 10. Just focus on the breath. Find time to do this once or twice a day. |
| 78 | Elimination | Congee (the Chinese version of oatmeal) is a great way to boost your metabolism and heal your digestive system. Try it for breakfast this week! |
| 79 | Elimination | |
| 80 | Elimination | Congee (the Chinese version of oatmeal) is a great way to boost your metabolism and heal your digestive system. Try it for breakfast this week! |

Rows 74-77 are grouped as 1219. Rows 78-80 are grouped as 1220.

FIG. 12D (Cont.)

| trigger_id (1301) | trigger_comparison (1302) | trigger_field (1303) | period (1304) | trigger_name (1305) |
|---|---|---|---|---|
| 1 | "!=" | Clot | OnToday | Clotting in Cycle |
| 2 | ">" | ClotCountThisCycle | OnToday | Clots Higher Than Last Cycle |
| 3 | "<" | ClotCountThisCycle | OnToday | Clots Lower Than Last Cycle |
| 4 | "==" | Cramp | OnToday | Mild Cramping |
| 5 | "==" | Cramp | OnToday | Medium Cramping |
| 6 | "==" | Cramp | OnToday | Severe Cramping |
| 7 | ">" | CrampThisCycle | OnToday | PMS Worse This Cycle |
| 8 | "<" | CrampThisCycle | OnToday | PMS Better This Cycle |
| 9 | "<=" | Volume | OnToday | High Volume |
| 10 | ">=" | Volume | OnToday | Low Volume |
| 11 | "<" | VolumeAvgDeviationThisCycle | OnToday | Improved Volume |
| 12 | ">" | VolumeAvgDeviationThisCycle | OnToday | Worsened Volume |
| 13 | "==" | Color | OnToday | Pale Blood |
| 14 | "==" | Color | OnToday | Fresh Red Blood |
| 15 | "==" | Color | OnToday | Deep Red Blood |
| 16 | "==" | Color | OnToday | Rusty Blood |
| 17 | "==" | Color | OnToday | Blue Blood |
| 18 | "==" | Color | OnToday | Black Blood |
| 19 | "==" | Discharge | OnToday | Cervical Fluid Present |
| 20 | "==" | CervicalFluidInCycle | FromCD19 | No Cervical Fluid in Cycle |
| 21 | "contains" | PMS Symptoms | OnToday | Breast tenderness |
| 22 | "contains" | PMS Symptoms | OnToday | Bloating or Gas |
| 23 | "contains" | PMS Symptoms | OnToday | Irritability |
| 24 | "contains" | PMS Symptoms | OnToday | Fatigue |
| 25 | "contains" | PMS Symptoms | OnToday | Headaches |
| 26 | "contains" | PMS Symptoms | OnToday | Low back Pain |
| 27 | ">" | FollicularTempAvgLastCycle | FromCD5 | High Follicular Avg Temp |
| 28 | "<" | FollicularTempAvgLastCycle | FromCD5 | Low Follicular Avg Temp |
| 29 | ">=" | FollicularTempVolatilityLastCycle | FromCD5 | Volatile Follicular Temp |
| 30 | ">" | OvulationDay | OnToday | Late Ovulation |
| 31 | "<" | OvulationDay | OnToday | Early Ovulation |
| 32 | "<" | LutealTempAvgLastCycle | FromCD15 | Low Luteal Temp |
| 33 | ">=" | LutealTempVolatilityLastCycle | FromCD15 | Volatile Luteal Temp |
| 34 | "==" | LutealTempSpikeAndDropLastCycle | FromCD15 | Spike and Drop Luteal Temp |
| 35 | "<=" | Sleep | OnToday | Sleep at 3 or Less |

FIG. 13A

| trigger_event | Notes | trigger_value |
|---|---|---|
| TrackingComplete | | "none" |
| BleedingStopped | ClotCount can use the score value we attribute to size of clot indicated to come up with a "Clot Score" for comparision | ClotCountLastCycle |
| BleedingStopped | ClotCount can use the score value we attribute to size of clot indicated to come up with a "Clot Score" for comparision | ClotCountLastCycle |
| TrackingComplete | | 1 |
| TrackingComplete | | 3 |
| TrackingComplete | | 5 |
| BleedingStarted | PMS can be calculated as score | CrampLastCycle |
| BleedingStarted | PMS can be calculated as score | CrampLastCycle |
| TrackingComplete | | 2 |
| TrackingComplete | | 8 |
| BleedingStopped | | VolumeAvgDeviationLastCycle |
| BleedingStopped | | VolumeAvgDeviationLastCycle |
| TrackingComplete | | "pale" |
| TrackingComplete | | "fresh" |
| TrackingComplete | | "deep" |
| TrackingComplete | | "rusty" |
| TrackingComplete | | "blue" |
| TrackingComplete | | "black" |
| TrackingComplete | | 1 |
| TrackingComplete | Check all tracking for cervical fluid in this cycle for "present" and if none occur it shoud trigger | 0 |
| TrackingComplete | | "breast tenderness" |
| TrackingComplete | | "gas/bloating" |
| TrackingComplete | | "irritability" |
| TrackingComplete | | "fatigue" |
| TrackingComplete | | "headaches" |
| TrackingComplete | | "low back pain" |
| AppLoaded | App Loaded should happen whenever app comes back up from being inactive | 97.4 |
| AppLoaded | App Loaded should happen whenever app comes back up from being inactive | 97.2 |
| AppLoaded | App Loaded should happen whenever app comes back up from being inactive | 0.15 |
| OnOvulationDetermined | | 14 |
| OnOvulationDetermined | | 14 |
| AppLoaded | | 98.2 |
| AppLoaded | | 0.15 |
| AppLoaded | | TRUE |
| TrackingComplete | | 3 |

FIG. 13A (Cont.)

| 36 | "==" | Sleep | OnToday | Sleep at 4 |
|---|---|---|---|---|
| 37 | "==" | Sleep | OnToday | Sleep at 5 |
| 38 | "==" | Sleep | OnToday | Sleep at 6 |
| 39 | "==" | Sleep | OnToday | Sleep at 7 |
| 40 | ">=" | Sleep | OnToday | Sleep at 8+ |
| 41 | "<=" | Water | OnToday | Water at 3 or Less |
| 42 | "==" | Water | OnToday | Water at 4 |
| 43 | "==" | Water | OnToday | Water at 5 |
| 44 | "==" | Water | OnToday | Water at 6 |
| 45 | "==" | Water | OnToday | Water at 7 |
| 46 | ">=" | Water | OnToday | Water at 8+ |
| 47 | "<=" | Veggies | OnToday | Veggies at 3 or Less |
| 48 | "==" | Veggies | OnToday | Veggies at 4 |
| 49 | "==" | Veggies | OnToday | Veggies at 5 |
| 50 | "==" | Veggies | OnToday | Veggies at 6 |
| 51 | "==" | Veggies | OnToday | Veggies at 7 |
| 52 | ">=" | Veggies | OnToday | Veggies at 8+ |
| 53 | "<=" | Energy | OnToday | Energy at 1 or Less |
| 54 | "==" | Energy | OnToday | Energy at 2 |
| 55 | "==" | Energy | OnToday | Energy at 3 |
| 56 | "==" | Energy | OnToday | Energy at 4 |
| 57 | "==" | Energy | OnToday | Energy at 5 |
| 58 | "==" | Stress | OnToday | Stress at 5 |
| 59 | "==" | Stress | OnToday | Stress at 4 |
| 60 | "==" | Stress | OnToday | Stress at 3 |
| 61 | "==" | Stress | OnToday | Stress at 2 |
| 62 | "==" | Stress | OnToday | Stress at 1 |
| 63 | "contains" | Digestion | OnToday | Digestion - Bloating |
| 64 | "contains" | Digestion | OnToday | Digestion - Gas |
| 65 | "contains" | Digestion | OnToday | Digestion - Nausea |
| 66 | "contains" | Digestion | OnToday | Digestion - Heartburn |
| 67 | "contains" | Digestion | OnToday | Digestion - Stomach Ache |
| 68 | "contains" | Digestion | OnToday | Digestion - It's all good |
| 69 | "==" | Sleep Trouble | OnToday | Trouble Falling Asleep |
| 70 | "==" | Sleep Trouble | OnToday | Trouble Staying Asleep |
| 71 | "==" | Sleep Trouble | OnToday | Sleep Pretty Good |
| 72 | "==" | Mood | OnToday | Mood - Anger/Irritability |
| 73 | "==" | Mood | OnToday | Mood - Anxiety |
| 74 | "==" | Mood | OnToday | Mood - Joy |
| 75 | "==" | Mood | OnToday | Mood - Depressed |
| 76 | "==" | Mood | OnToday | Mood - Worried |
| 77 | "==" | Elimination | OnToday | Elimination - Loose |
| 78 | "==" | Elimination | OnToday | Elimination - Regular |
| 79 | "==" | Elimination | OnToday | Elimination - Constipation |
| 80 | ">" | PMS | OnToday | PMS Severity |
| 81 | "==" | Cramp | OnToday | Medium Cramping |
| 82 | "==" | Cramp | OnToday | Severe Cramping |
| 83 | "==" | Spotting | OnToday | Spotting |

FIG. 13B

| | | |
|---|---|---|
| TrackingComplete | | 4 |
| TrackingComplete | | 5 |
| TrackingComplete | | 6 |
| TrackingComplete | | 7 |
| TrackingComplete | | 8 |
| TrackingComplete | | 3 |
| TrackingComplete | | 4 |
| TrackingComplete | | 5 |
| TrackingComplete | | 6 |
| TrackingComplete | | 7 |
| TrackingComplete | | 8 |
| TrackingComplete | | 3 |
| TrackingComplete | | 4 |
| TrackingComplete | | 5 |
| TrackingComplete | | 6 |
| TrackingComplete | | 7 |
| TrackingComplete | | 8 |
| TrackingComplete | | 1 |
| TrackingComplete | | 2 |
| TrackingComplete | | 3 |
| TrackingComplete | | 4 |
| TrackingComplete | | 5 |
| TrackingComplete | | 5 |
| TrackingComplete | | 4 |
| TrackingComplete | | 3 |
| TrackingComplete | | 2 |
| TrackingComplete | | 1 |
| TrackingComplete | | "bloating" |
| TrackingComplete | | "gas" |
| TrackingComplete | | "nausea" |
| TrackingComplete | | "heartburn" |
| TrackingComplete | | "stomach ache" |
| TrackingComplete | | "it's good!" |
| TrackingComplete | | "trouble falling asleep" |
| TrackingComplete | | "trouble staying asleep" |
| TrackingComplete | | "pretty good" |
| TrackingComplete | | "irritable/anger" |
| TrackingComplete | | "anxious" |
| TrackingComplete | | "happy/joy" |
| TrackingComplete | | "depressed" |
| TrackingComplete | | "worried" |
| TrackingComplete | | "loose stool" |
| TrackingComplete | | "regular/ formed" |
| TrackingComplete | | "constipation" |
| TrackingComplete | | 0 |
| TrackingComplete | | 2 |
| TrackingComplete | | 4 |
| BleedingStart | | "yes" |

FIG. 13B (Cont.)

| TriggerEvent | Period | TriggerField |
|---|---|---|
| AppLoaded | OnToday | Color |
| BleedingStarted | FromCD1 | Discharge |
| BleedingStopped | FromCD2 | CervicalFluidInCycle |
| OnOvulationDetermined | FromCD3 | Clot |
| TrackingComplete | FromCD4 | ClotCountLastCycle |
| | FromCD5 | ClotCountThisCycle |
| | FromCD6 | CrampThisCycle |
| | FromCD7 | CrampLastCycle |
| | FromCD8 | Cramp |
| | FromCD9 | Digestion |
| | FromCD10 | Elimination |
| | FromCD11 | Energy |
| | FromCD12 | FollicularTempAvgLastCycle |
| | FromCD13 | FollicularTempVolatilityLastCycle |
| | FromCD14 | LutealTempAvgLastCycle |
| | FromCD15 | LutealTempSpikeAndDropLastCycle |
| | FromCD16 | LutealTempVolatilityLastCycle |
| | FromCD17 | Mood |
| | FromCD18 | Ovulation |
| | FromCD19 | PMS |
| | FromCD20 | PMSSeverityAvgLast2Cycle |
| | FromCD21 | PMSSeverityAvgLastCycle |
| | FromCD22 | PMS Symptoms |
| | FromCD23 | Sleep |
| | FromCD24 | Sleep Trouble |
| | FromCD25 | Spotting |
| | FromCD26 | Stress |
| | FromCD27 | Veggies |
| | FromCD28 | Volume |
| | | VolumeAvgDeviationLastCycle |
| | | VolumeAvgDeviationThisCycle |
| | | Water |

FIG. 14

CONCEIVABLE BASAL BODY TEMPERATURES AND MENSTRUAL CYCLE

CROSS-REFERENCE TO RELATED APPLICATIONS

None.

FIELD

The present invention is generally related to fertility, and more particularly, to software programs, systems and methods for increasing the chances of conception by combining best practices as described by current medical literature for fertility changes along with herbal recommendations to address any underlying fertility issues to move toward an ideal fertility state for each individual user.

BACKGROUND

Basal body temperature ("BBT") charting has been a popular method for natural family planning and ovulation prediction for the last 40 years. Currently there are many applications, for example smart phone Applications that use technology to collect and aggregate this BBT data. The information gleaned from temperature changes across the menstrual cycle can highlight a surge in luteinizing hormone (LH) which is an early predictor of ovulation. This data is limited in its usefulness because it can only predict ovulation, but there are many other aspects of the BBT that can be useful in highlighting other important subclinical factors that can impact a woman's ability to conceive. Conventional thinking assumes that if the BBT chart is biphasic and has a 1-3 tenth of a temperature drop at ovulation, the chart is considered normal. Additionally, these applications largely ignore menstrual parameters as measures to indicate subclinical indicators of a sub-fertile state. Absent was a method for a woman to use technology to collect, aggregate and assess BBT info and essential menstrual parameters as indicators of overall fertility or fertility potential.

Some existing applications have attempted to improve the accuracy of ovulation prediction by adding BBT charting to the collection of other symptoms like cervical discharge, cervical height and mood.

These solutions still fail to utilize important and highly relevant BBT and menstrual cycle data that can be used to reveal underlying fertility issues. Identifying the exact timing of ovulation is very useful for women who are fertile, but who do not know when to have intercourse. But for women who have identified clinical or subclinical fertility issues, this data is insufficient to be a resource for improving their fertility.

Thus there is a need for alternative strategies and regimes to increase fertility by moving a user's personalized fertility state toward an ideal fertility state.

SUMMARY

It is an object of the invention to maximize a user's fertility potential by providing a software program, such as the Conceivable™ software program, that combines a proprietary methodology for identifying the underlying causes of infertility with the proven use of herbal formulas, and intelligent, personalized wellness recommendations that give the individual user the power to improve their natural fertility without costly intervention.

For a user to reach their maximum fecundity, the Conceivable™ software program uses user provided information to provide a user's Conceivable™ potential score 1000, shown in FIG. 10. The Conceivable™ potential score accumulates a variety of fertility metrics, described herein, that the user tracks in the Conceivable™ software program, and measures the improvements in key lifestyle, BBT, and menstrual cycle metrics. The Conceivable™ software program focuses on a number of health factors, including: Conceivable™ hurdles 1001, Basal Body Temperature 1002, cycle health 1003, lifestyle 1004 and herbal formulas 1005.

For the Conceivable™ hurdles, the inventors analyzed data from over 7,000 women and discovered five critical fertility hurdles the user's body must clear in order to conceive that compromise fecundability. The use of the Conceivable™ software program identifies the user's hurdles and creates a personalized plan to steadily remove the user's roadblocks to increase users' propensity to conceive.

For the Basal Body Temperature ("BBT"), the Conceivable™ software program goes beyond using BBT as an ovulation predictor. The inventors identified a specific BBT curve that is ideal for conception. The use of the Conceivable™ software program helps the user understand the relationship between their BBT and their propensity to conceive, and adjusts their temperatures into their ideal range.

For the cycle health, various characteristics of the user's menstrual cycle provide strong signals related to their natural fertility. The Conceivable™ software program helps them measure these factors, understand how they relate to their reproductive health, and take proactive steps to improve them.

For lifestyle, factors like hydration, sleep and diet are the most important things user can control to improve their fertility. The Conceivable™ software program helps them make the right choices every day to maximize their fertility, based on the Conceivable™ software program's assessment of user entered data.

The herbal formulas are one of the key items to maximize user's fertility. Users using the Conceivable™ software program have access to a unique and powerful line of herbal formulas that the Conceivable™ software program formulates and recommends especially for the individual users. The Conceivable™ software program in combination with the herbal formulas helps users move toward their maximum fecundity.

BRIEF DESCRIPTION OF THE DRAWINGS

These and other features, aspects and advantages of the present application are described with reference to drawings of certain embodiments, which are intended to illustrate, but not to limit, the various inventions disclosed herein. It is to be understood that the attached drawings are for the purpose of illustrating concepts and embodiments of the present application and may not be to scale.

FIG. 7 shows an erratic BBT chart in the luteal phase.

FIGS. 11A-11E show various worksheets used as input for the Conceivable™ formulas. This information is used in the Conceivable™ formula algorithm to interpret the collected data and to recommend actionable changes for the individual users to improve their fertility cycle FIGS. 12A-12D show example recommendations the user can make for a number of conditions, include clotting, cramping, volume, color, ovulation, cervical fluid, PMS severity, PMS symptoms, spotting, follicular temperature, luteal temperature, sleep, water, veggies, energy, stress, digestion, sleep quality, mood and elimination.

FIGS. 13A-13B show one example of the triggers that may be experienced by the user.

FIG. 14 shows one example of a menstrual cycle of 28 cycle days ("CD") long, including the trigger event, period and the trigger field.

DETAILED DESCRIPTION

Figure 1:
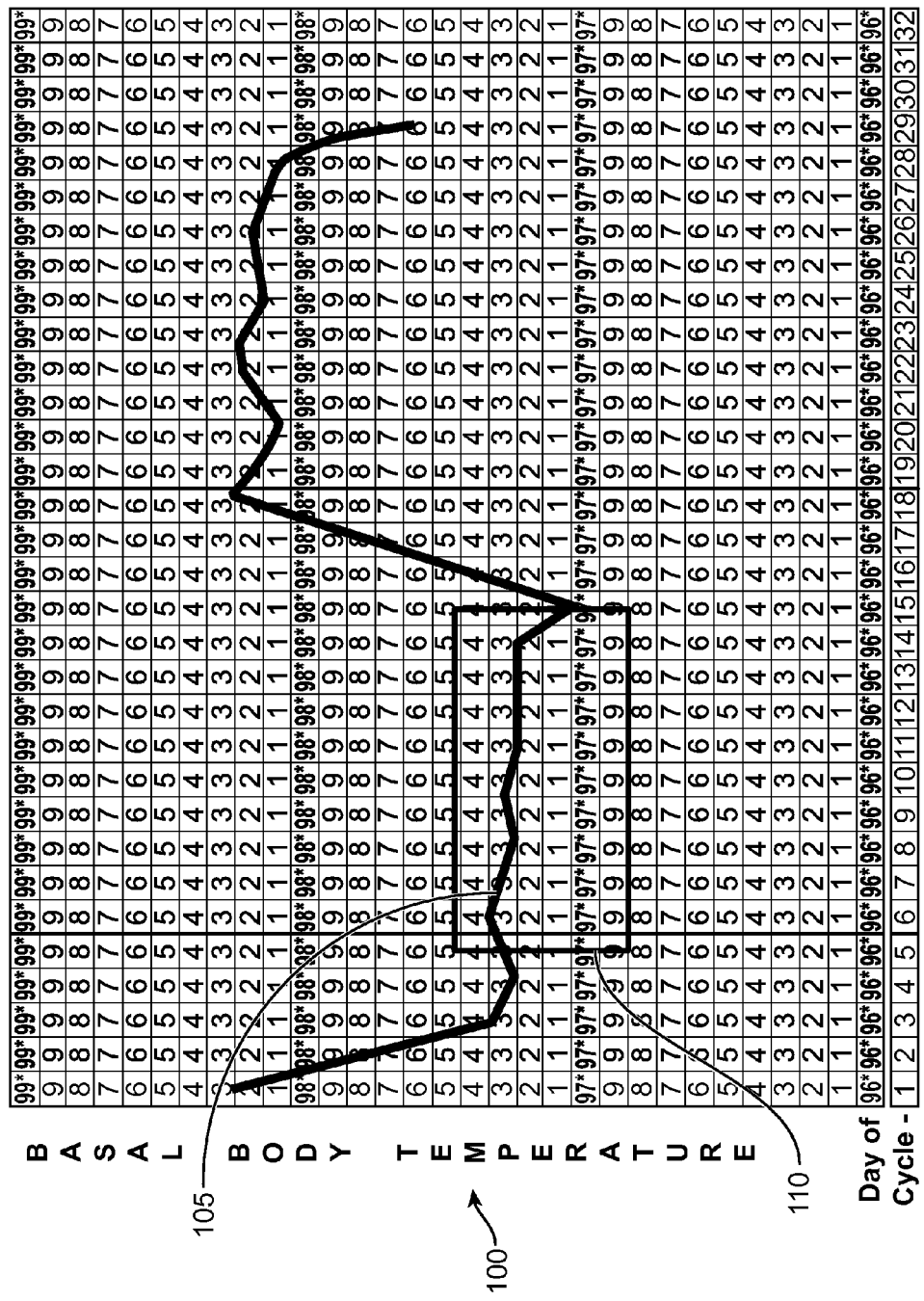
FIG. 1 shows an example of an ideal chart in which the temperatures remain stable throughout the body of the follicular phase.

The ideal menstrual cycle for conception combines certain basal body temperature and menstrual cycle parameters. The applicants have termed this ideal menstrual cycle description as "The Conceivable Basal Body Temperatures and Menstrual Cycle" and disclosed some embodiments and examples of some ideal parameters in the application. Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments and examples described herein, but should be determined only by a fair reading of the claims that follow.

Embodiments of the invention will now be described with reference to the figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The Conceivable Basal Body Temperatures and Menstrual Cycle

Basal body temperature ("BBT") reflects hormone function and underlying issues that impact a woman's fertility. When BBT's average 97.3 degrees F. for the first 14 days of the cycle and 98.2 degrees F. after ovulation, a woman's fertility potential is optimized. Any percentage deviation from these norms may indicate a larger issue.

An ideal menstrual cycle is 28 cycle days ("CD") long, with ovulation occurring on CD 14, with stretchy, abundant, clear cervical discharge, no PMS, bleeding that last 4 days (no more, no less) with fresh red blood, absent of clotting, and with no accompanying cramping.

The inventors have developed a software program ("The Conceivable Software Program") that uses technology to aggregate basal body temperature taken by the user with the aforementioned menstrual parameters to identify the subclinical issues that may be impacting her fertility.

The current solutions described in the Background use technology in a very limited fashion that may only track basal body temperatures, cervical discharge, cervical height and mood to predict ovulation. That is their only offering. By only looking at the temperature differential around ovulation, many opportunities are lost to collect valuable data that can actually direct the user to take very specific action to improve the factors that are impacting their fertility.

The Conceivable Software Program

The Conceivable Software Program is more than an ovulation tracker. The Conceivable Software Program is a powerful application that helps the user identify and address underlying issues that may be preventing them from conceiving and uses the deviations from a prescribed "ideal fertility state" to determine the subclinical factors impacting a woman's fertility.

The Conceivable Software Program is unique and proprietary for several reasons. The invention is the first to use BBT's and menstrual parameters as an assessment tool/prognostic indicator for a women's fertility. The Conceivable Software Program is also the first to develop an algorithm to interpret the collected data and to recommend actionable changes by combining best practices as described by current medical literature and herbal formulas to make changes for the user. The Conceivable Software Program combines recommendations of best practices as described by current medical literature for changes (see FIGS. 12A-12E) along with herbal recommendations (see FIG. 9) to address the underlying fertility issues to move toward the ideal fertility state.

The Conceivable Software Program is personalized care, outside the clinic. As the user shares data with the Conceivable Software Program, they'll receive personalized recommendations, lifestyle guidance, herbal recommendations and accountability reminders, helping them make steady progress.

The Conceivable Software Program is a mobile application that can be installed on many portable electronic devices, from portable computers to smartphones (such as androids or i-phones/i-pads). The Conceivable Software Program helps the user reach their maximum fertility by using the information input by the user, as described above, combined with the personalized herbal formulas identified and recommended by the software program for the individual user, as well as lifestyle recommendations.

The Conceivable Software Program will motivate and inspire the user, by showing them the progress they are making toward maximum fertility. It's easy to monitor their improvement each day, and from cycle to cycle.

The Conceivable Software Program allows the user to understand the connections of fertility. By capturing lifestyle data and key fertility metrics in a single application, the Conceivable Software Program helps the user clearly understand how their lifestyle choices affect their ability to conceive, and empowers them to take action that maximizes the user's natural fertility.

The Conceivable Software Program may be also be integrated with fertility acupuncture care and/or other complementary, alternative, holistic, or allopathic fertility care and/or wellness providers and/or clinics. The Conceivable Software Program may be offered through fertility acupuncture clinics. The Conceivable Software Program Conceivable technology makes it easy for the user to capture the fertility, menstrual and wellness metrics that matter most to the care they receive at their fertility acupuncture clinic.

The Conceivable Software Program uses the deviations from a prescribed "ideal fertility state" to determine the subclinical factors impacting a woman's fertility. One example of an ideal fertility state consists of:
  a 28 day menstrual cycle days ("CD")
  ovulation occurring on CD 14
  abundant, clear, stretchy, cervical discharge on CD 14
  absence of Premenstrual syndrome ("PMS")
  4 days of menstrual bleeding
  enough menstrual blood to soak a tampon or pad every 4 hours
  no pain, cramping, clotting or spotting before, during, or after period
  Basal body temperature (BBT):
    CD 4-14 temperatures need to average 97.3 degrees F. with a standard deviation of less than 0.1 degrees F.
    CD 17-28 temperatures need to average 98.2 degrees F. or higher with a standard deviation of less than 0.01 degrees F.

An Explanation of BBT as it Relates to an Ideal Fertility State.

Follicular Phase:

The follicular phase is the first part of the ovarian cycle. During this phase, the ovarian follicles mature and get ready to release an egg.

FIG. 1 shows an example of an ideal chart 100 in which the Basal Body Temperatures ("BBT") 105 remain stable throughout the body of the follicular phase 110. The BBT should fall within 97.2-97.4 degrees F. In this range, good quality eggs are produced along with abundant, clear, and stretchy (fertile) cervical fluid. Temperatures that fall outside this range can be corrected through lifestyle and herbal interventions.

Figure 2:
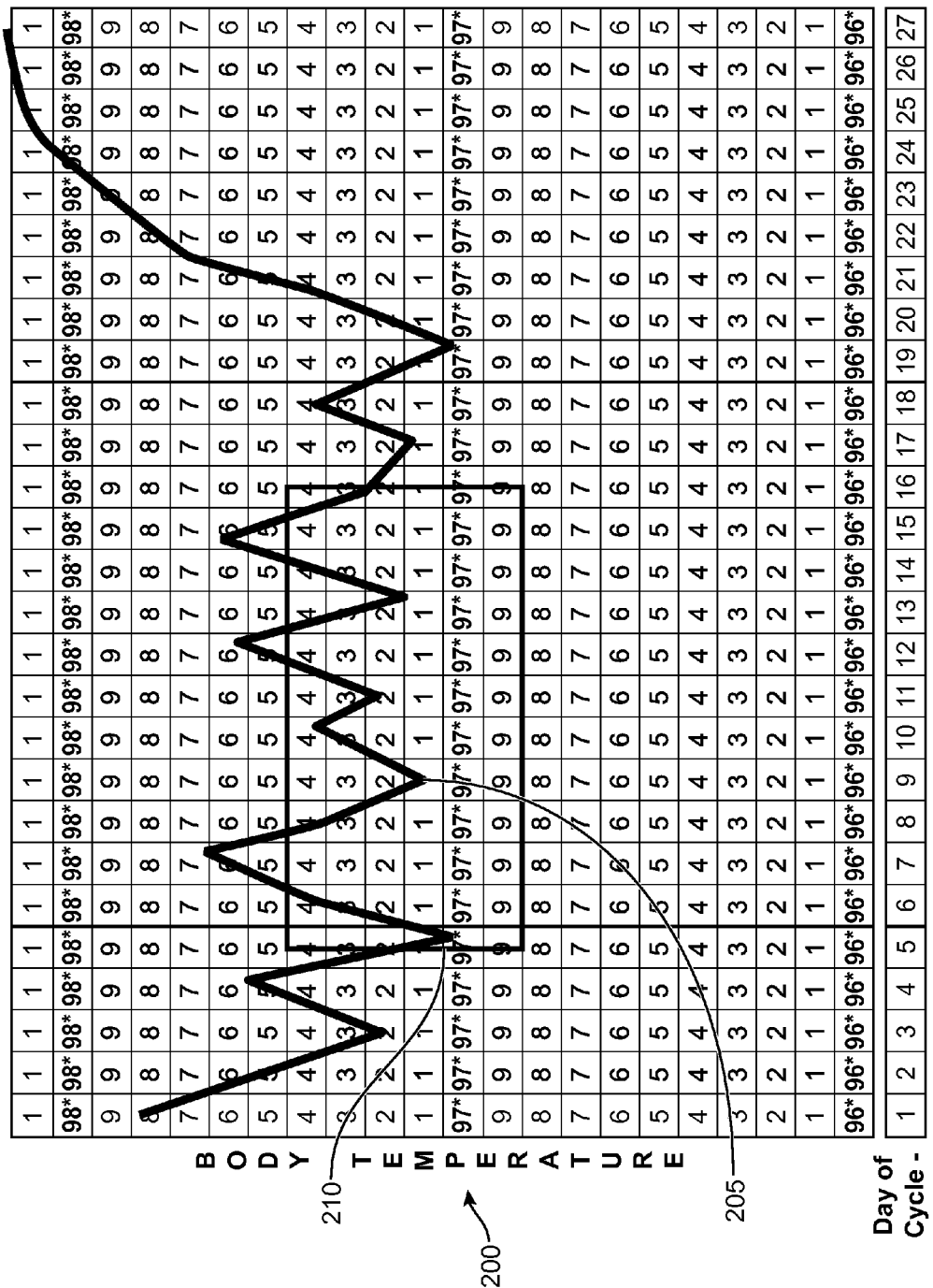
FIGS. 2 and 3 show charts that demonstrate pathological departures from an ideal, fertile basal body temperature state shown in FIG. 1.
Figure 3:
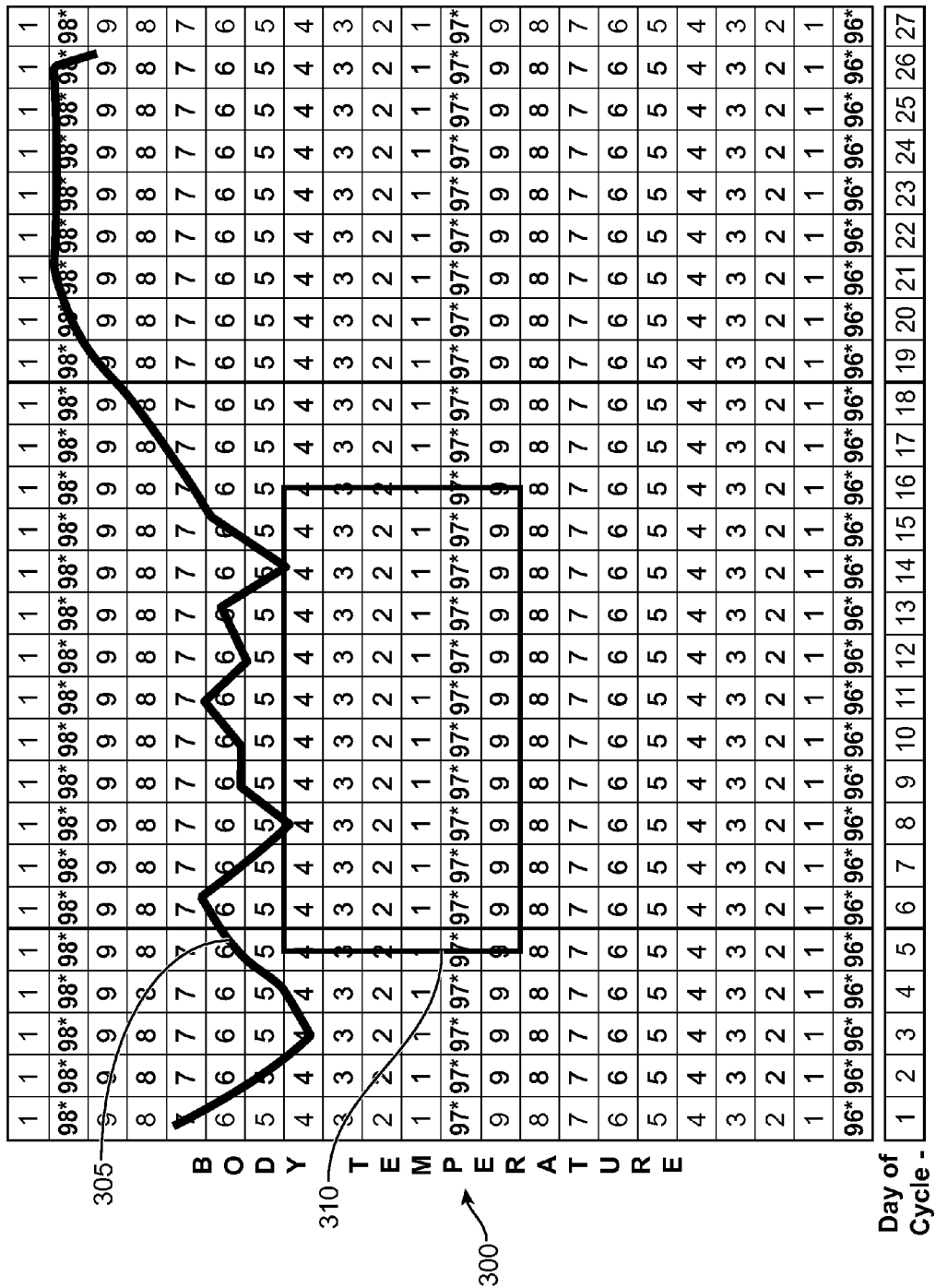

FIGS. 2 and 3 show charts that demonstrate pathological departures from an ideal, fertile BBT state described above in FIG. 1.

FIG. 2 shows an erratic chart 200 where BBT 205 varies wildly and ovulation occurs late in the follicular phase 210. This is a common pattern for women who experience irregular ovulation and is a good indicator for hormonal imbalance, specifically the interaction between estradiol and follicle-stimulating hormone ("FSH"). This is also a common pattern for women who suffer from Polycystic ovary syndrome (PCOS).

FIG. 3 shows a chart 300 with an elevated BBT 305 in the follicular phase 310. Elevated temperatures in this phase are associated with poor egg quality, scanty cervical fluid, and elevated levels of FSH and poor ovarian response or diminished ovarian reserve.

Luteal Phase:

The luteal phase is the latter phase of the ovarian cycle. The main hormone associated with this phase is progesterone. During the luteal phase progesterone production must be sufficient to stabilize the uterine lining and allow implantation of the fertilized embryo to occur.

Figure 4:
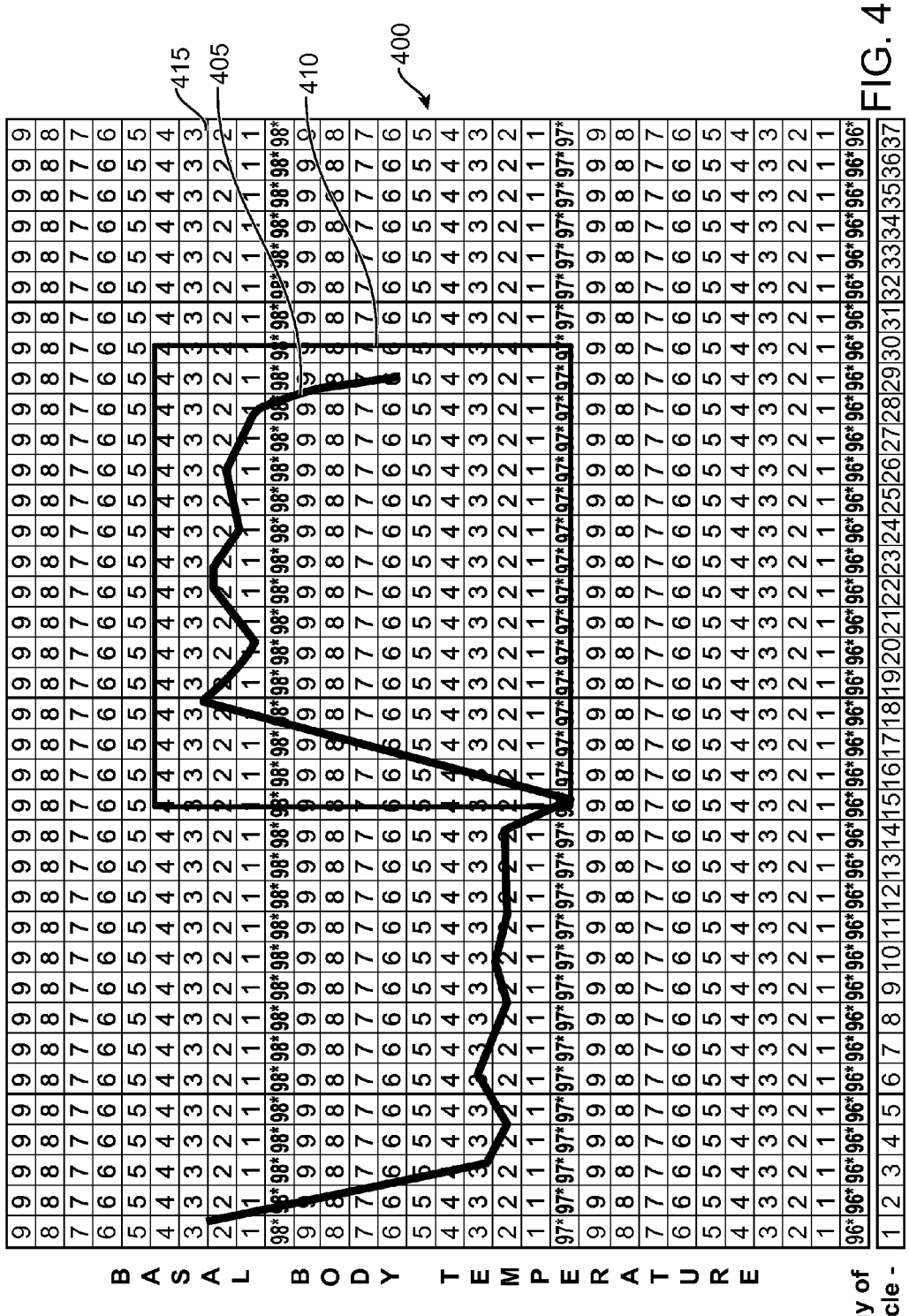
FIG. 4 shows an example of an ideal chart for the BBT state for the luteal phase in which the temperatures to climb quickly after ovulation to an average of 98.2 degrees F.

FIG. 4 shows an example of an ideal chart 400 for the BBT state for the luteal phase 410 in which the BBT 405 climbs quickly after ovulation to an average of 98.2 degrees F. 415. Temperatures that consistently fall below this ideal average indicate insufficient progesterone function. Insufficient progesterone leads to lower pregnancy rates and higher miscarriage rates. BBT's lower than ideal can be corrected through a combination of lifestyle and herbal interventions (as discussed below).

Figure 5:
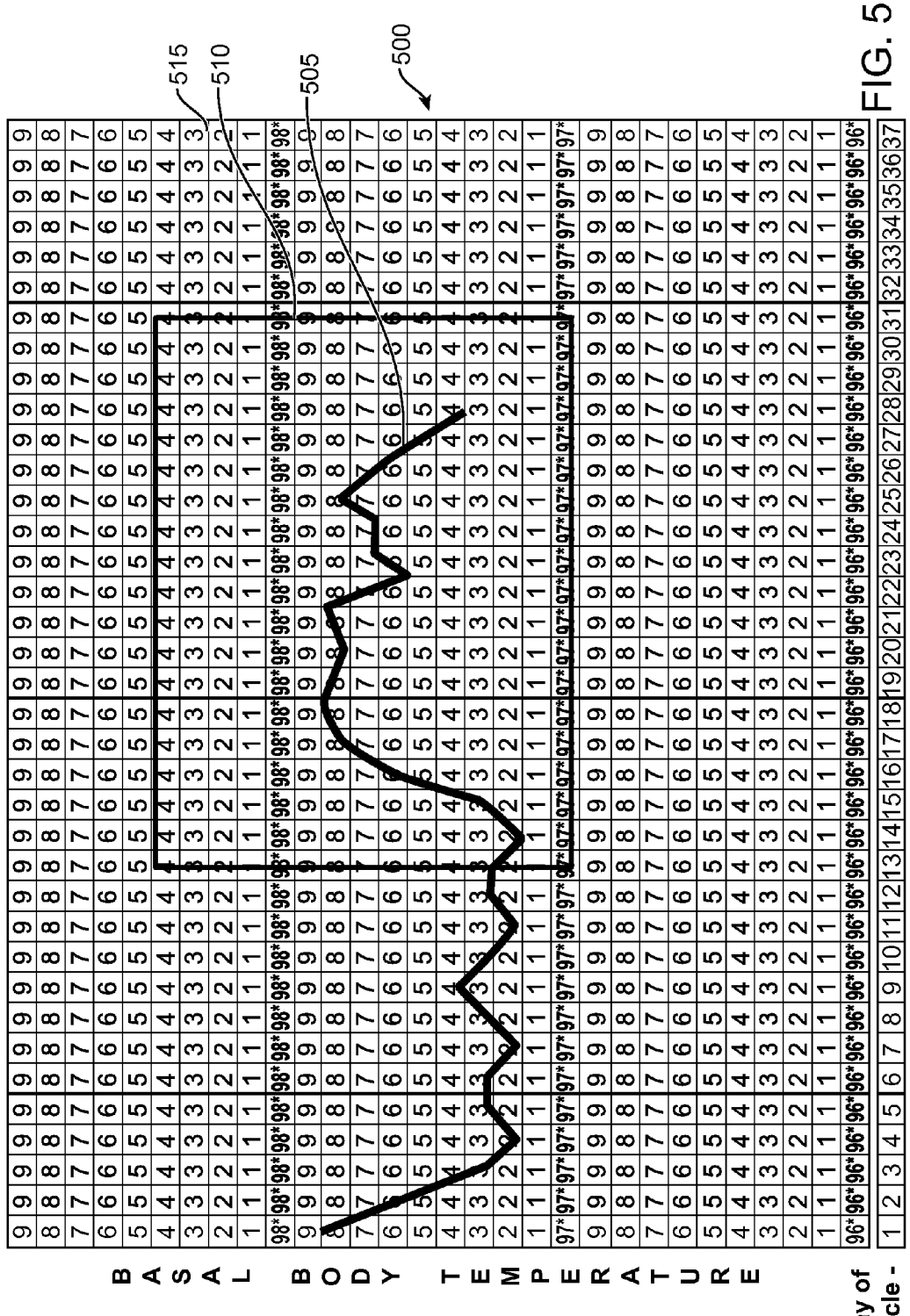
FIG. 5 shows a chart that demonstrates pathological departures from an ideal, fertile basal body temperature state shown in FIG. 5.

FIG. 5 shows a chart 500 that demonstrates pathological departures from an ideal, fertile BBT state. This chart demonstrates a pattern in which the BBT 505 fails to rise to an appropriate level 515 (98.2 degrees F. or higher) for the luteal phase 510. This can indicate a progesterone deficiency that is associated with decreased fecundability and higher miscarriage rates.

Figure 6:
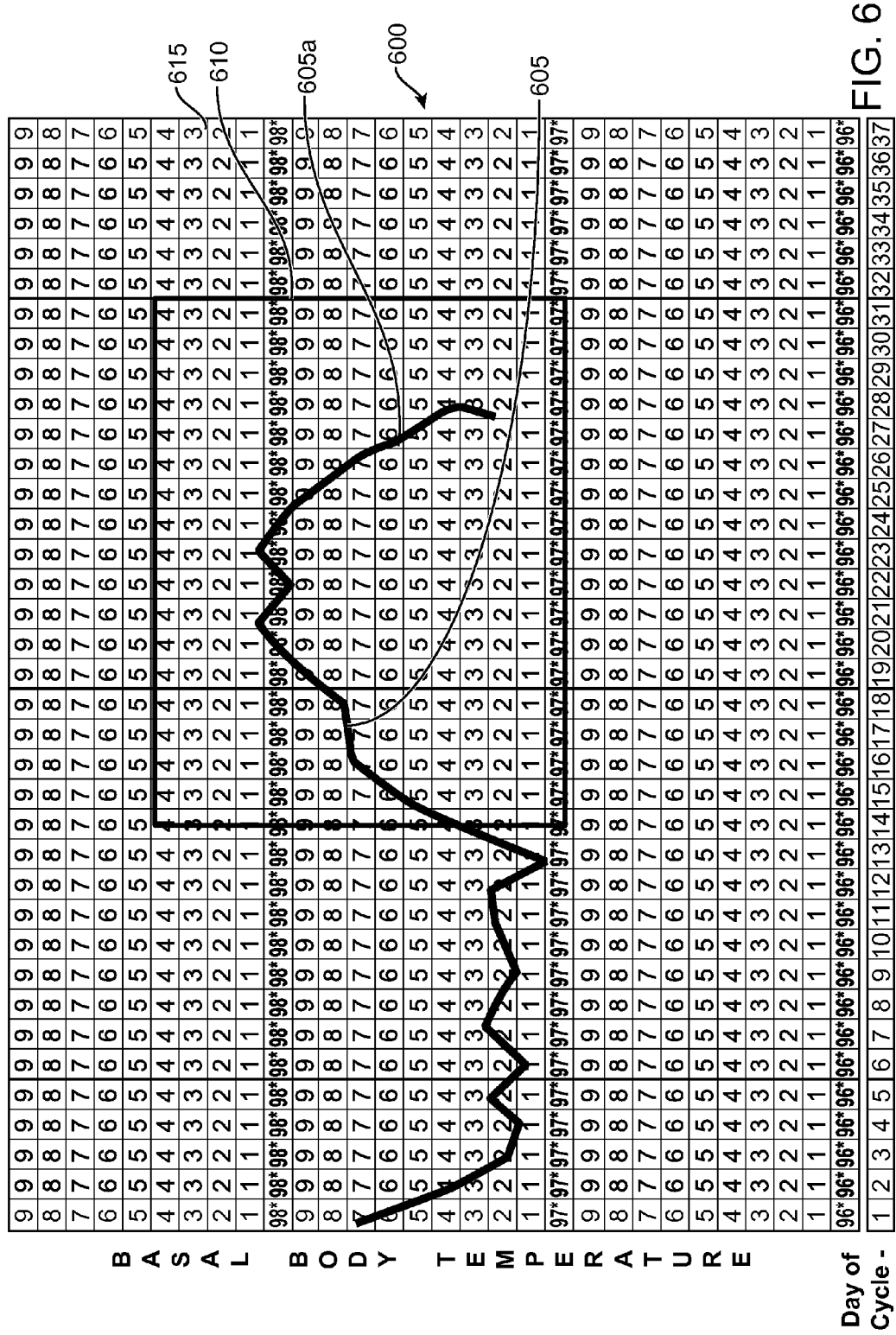
FIG. 6 shows a chart that demonstrates a pattern in which BBT rises to an appropriate level, but fails to maintain that level throughout the luteal phase.

FIG. 6 shows a chart 600 that demonstrates a pattern in which BBT 605 rises to an appropriate level 615, but fails to maintain that level throughout the luteal phase 610. This fall in BBT 605a is associated with a fall in progesterone levels and can lead to early term miscarriage or implantation failure. This type of pattern may also result in premenstrual spotting.

Figure 7:
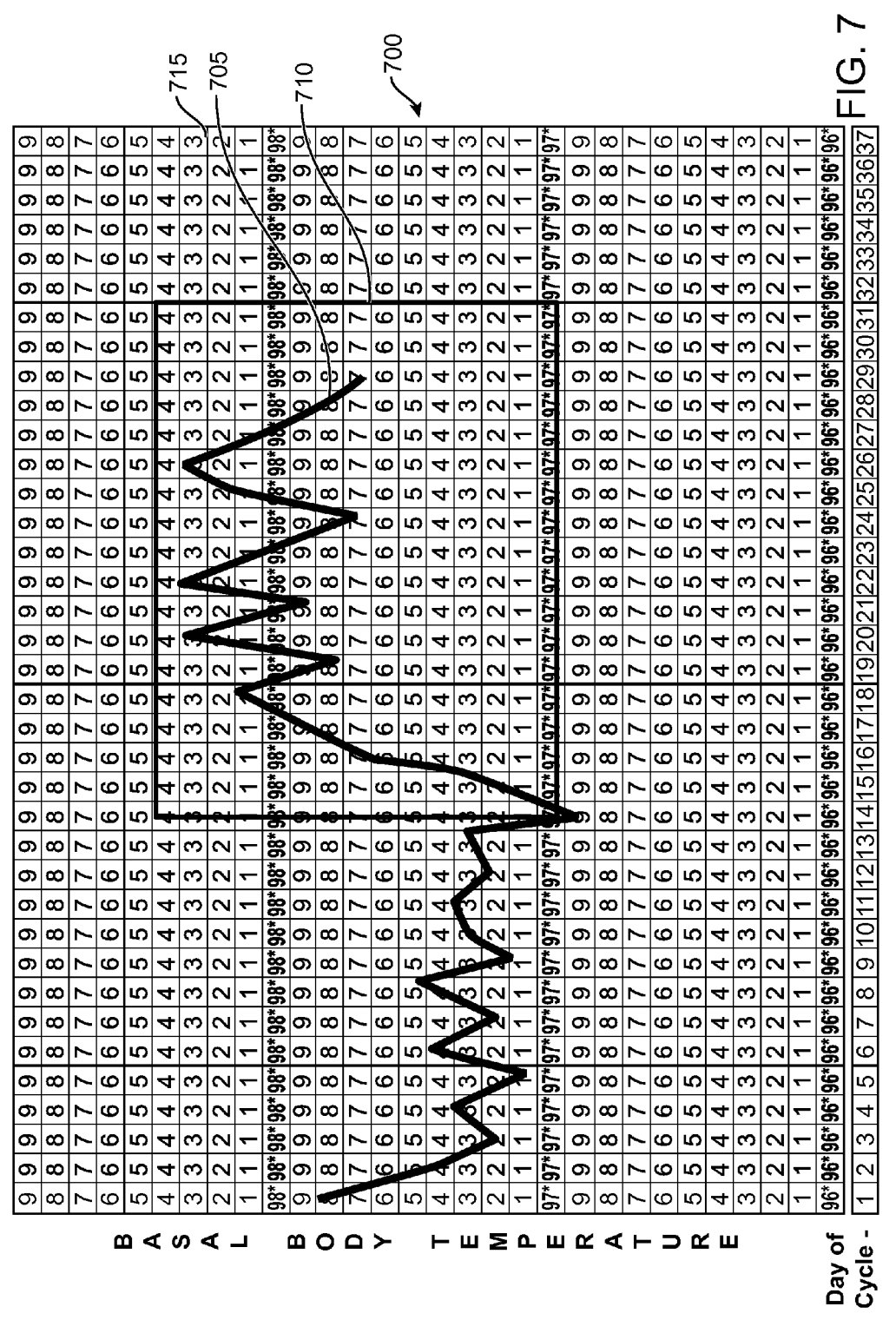

FIG. 7 shows an erratic BBT chart 700 in the luteal phase 710. This erratic BBT 705 demonstrates a pattern of hormonal imbalance that is generally associated with PMS.

By assessing BBT patterns, the Conceivable Software Program identifies subclinical patterns of infertility and offers interventions that can address these patterns.

The Conceivable Software Program Assessment process.
1. The Conceivable Software Program prompts user to report on the state of the aforementioned conditions, as shown in the charts. The Conceivable Software Program uses a proprietary scale to determine the user's personalized fertility state to score the severity of the deviations from the ideal fertility state. The user inputs data in the software program, for example, menstrual parameters, lifestyle factors, and BBT's.
2. By algorithmically assessing the collected data, the software can identify subclinical factors and their causes that inhibit a woman's fertility. The data may include, but is not necessarily limited to, high, low, or erratic BBT across the menstrual cycle, menstrual clotting, menstrual pain, insufficient menstrual flow, hemorrhagic menstrual flow, insufficient cervical discharge, irregular ovulation, symptoms associated with PMS such as bloating, irritability, headaches, breast tenderness, and cramping, and spotting.
3. Once the data has been aggregated, the software assigns the user a "Hurdle" or "Hurdles" of one or more symptoms that represent the underlying cause for the subclinical factors.
   The Hurdles and their main associated symptoms are:
   Hot—high follicular phase basal body temperatures, scanty cervical discharge, insomnia (harder to stay asleep).
   Cold—low luteal phase basal body temperatures, cold hands and feet, frequent urination Stuck—PMS, erratic temperatures across the cycle, irritability Pale—scanty menstrual blood, anxiety, pale skin Tired—fatigue, gas and bloating, loose stools, weight gain or retention The Conceivable Software Program Hurdle Functions.

4. After the User Hurdle or Hurdles are assigned, the software program recommends herbal formulas according to the phases of the menstrual cycle to support fertility wellness. Examples of the goal for each phase may include the following:

Bleeding—Remove old, clotty, or stale uterine lining through menstrual bleeding, decrease menstrual pain, improve uterine blood flow, support production of a healthy amount of uterine bleeding.

Follicular—Regulate BBT, build a healthy and sufficient new uterine lining, regulate ovulation, promote a healthy environment for follicular development and egg maturation.

Luteal—Regulate BBT, enhance progesterone function, stabilize uterine lining, maintain pregnancy.

The Conceivable Software Program Herbal Recommendations.

5. Once the User Hurdle function is complete, the software program calculates a "Conceivable Potential Score" based on the menstrual parameters, BBT's, and lifestyle behaviors. The Conceivable Software Program makes herbal recommendations based on the Hurdle or Hurdles to address the underlying fertility issues to move the user's personalized fertility state toward the ideal fertility state. The user is fully engaged in all of the behaviors that have been demonstrated by the medical literature to make the biggest difference in fertility outcomes.

The Conceivable Software Program Fertility Scoring.

6. Every day the user should enter the new data so that the software can constantly recalculate their "Conceivable Potential Score" and provide feedback to the user to make any changes. The software has the ability to notice what the user is doing and not doing in terms of the recommendations and then can "push" education and suggestions to the user to facilitate positive behavior modification.

The Conceivable Software Program Personalized Lifestyle Interventions Based on Program Input.

7. The Conceivable Software Program may also have the ability to take the aggregated data and makes a customized wellness program that includes sleep, hydration, and nutrition specifically designed according to the users underlying causes or issues around their infertility.

Herbal System to Address the Underlying Fertility Issues to Move Toward the Ideal Fertility State.

The following description illustrates some examples of actionable changes the user may do to move their personalized fertility state toward the ideal fertility state using herbs exclusively selected for them to address their condition.

Figure 8:
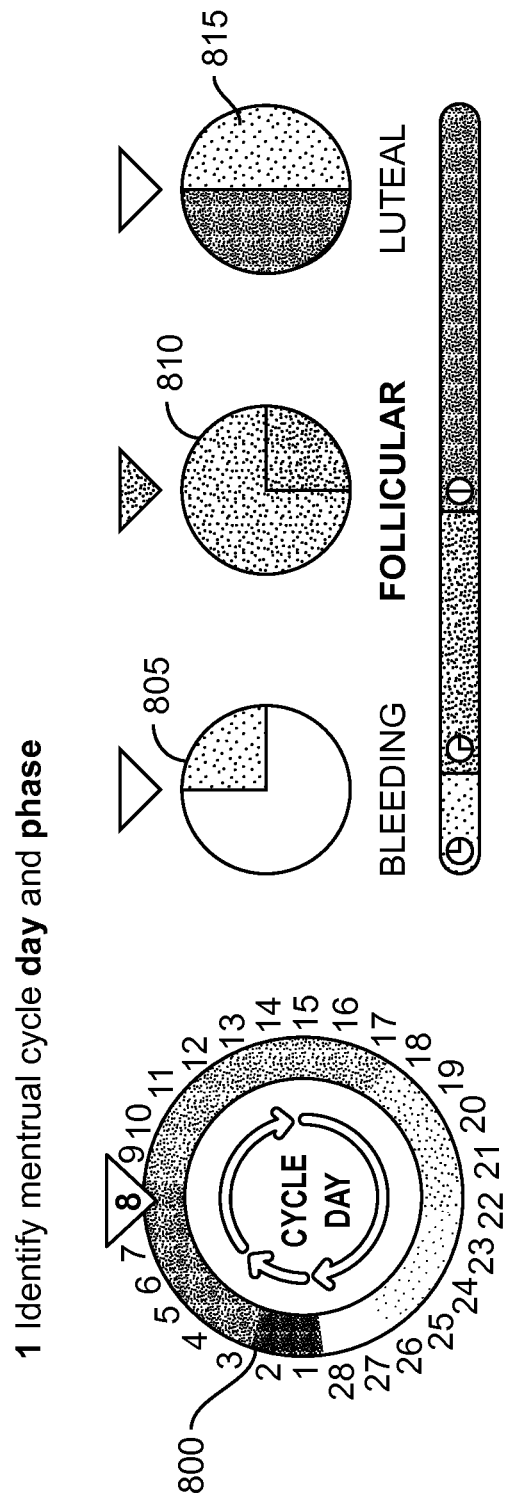
FIG. 8 shows how the user identifies the menstrual cycle day and phase, including, bleeding, follicular and luteal.

1. Identify menstrual cycle day and phase—The user identifies the menstrual cycle day and phase, as shown in FIG. 8 As discussed above, the phase is as follows:

Bleeding 805—Remove old, clotty, or stale uterine lining through menstrual bleeding, decrease menstrual pain, improve uterine blood flow, support production of a healthy amount of uterine bleeding.

Follicular 810—Regulate BBT, build a healthy and sufficient new uterine lining, regulate ovulation, promote a healthy environment for follicular development and egg maturation.

Luteal 815—Regulate BBT, enhance progesterone function, stabilize uterine lining, maintain pregnancy.

Figure 9:
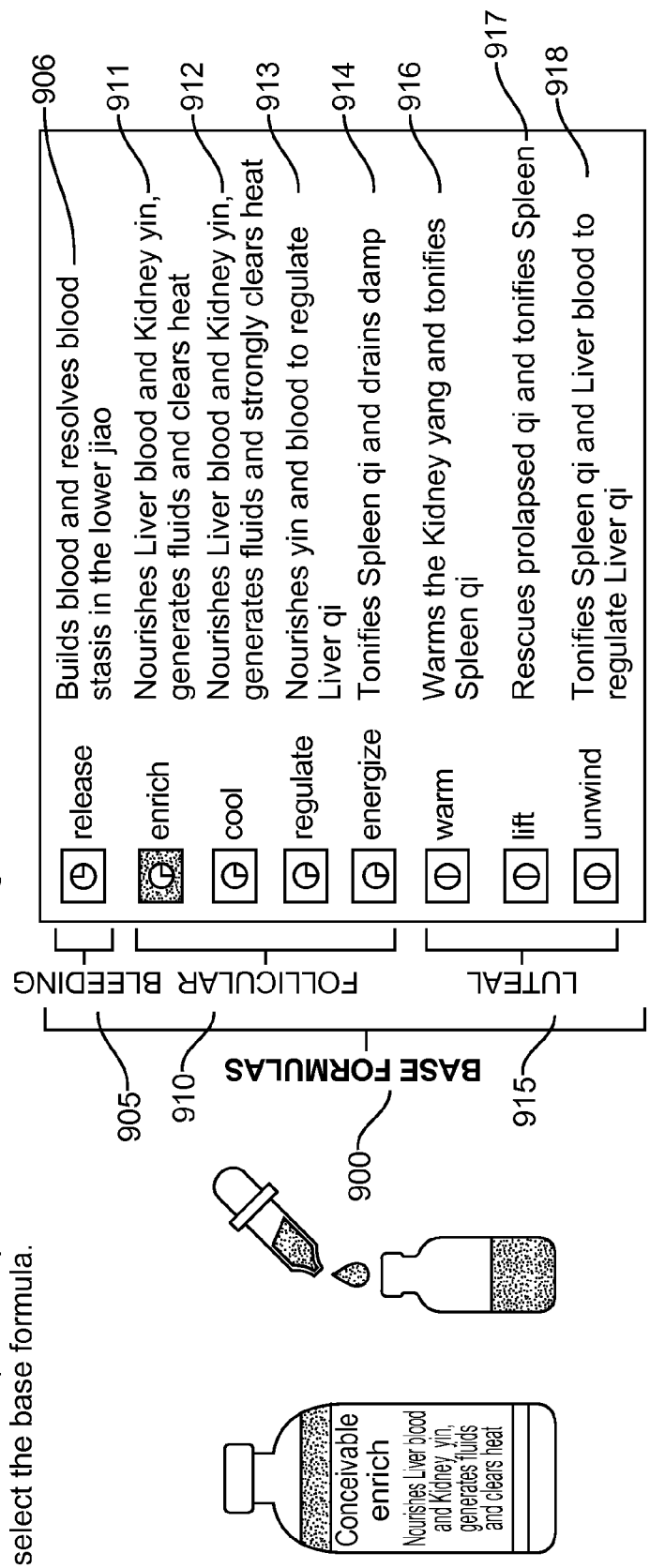
FIG. 9 shows the user selection of a base herbal formula selected to match the phases of bleeding, follicular, and luteal.
Figure 10:
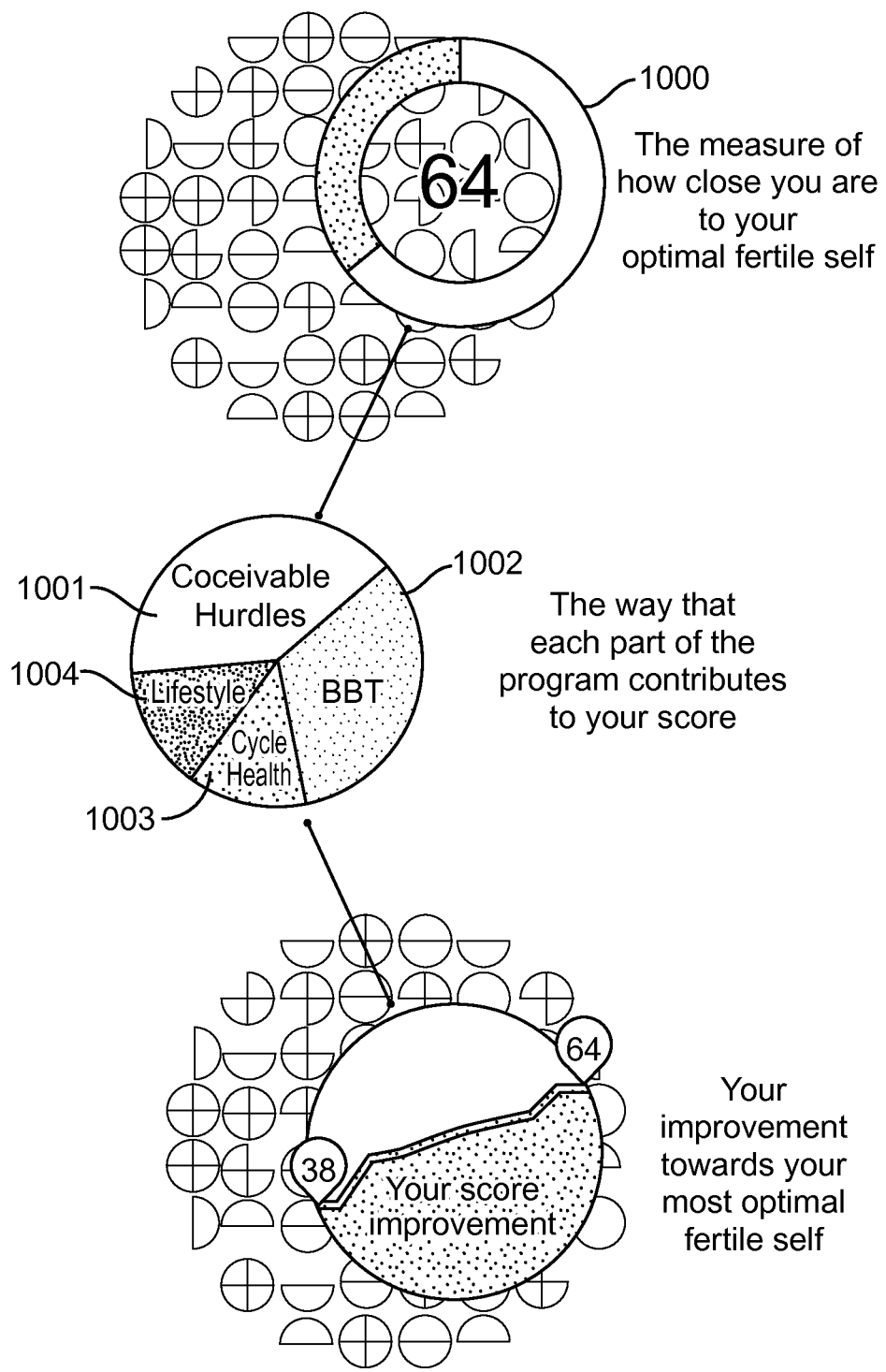
FIG. 10 shows one example of a Conceivable™ potential score from a variety of fertility metrics that the user tracks in the Conceivable™ software program, and measures the improvements they are making. The Conceivable™ software program focuses on a number of health factors, including: Conceivable™ hurdles, Basal Body Temperature, cycle health, lifestyle and herbal formulas.

2. Selection of a base herbal formula—Based on the user's cycle and Conceivable™ hurdles, a base herbal formula is identified and selected by the software program for the individual user 900 to match the phases, Bleeding 905, Follicular 910, and Luteal 915, as shown in FIG. 9. Below are some examples of some herbs that may be used for the base formulas.

For Bleeding 905, some examples of base herbal formulas may include:

Release 906—Builds blood and resolves blood stasis in the lower jiao.

| Release | | |
|---|---|---|
| Pin Yin | Latin | English Common |
| Shu Di Huang | Radix Rehmanniae | Cooked *Rehmannia* |
| Dang Gui | Radicis Angelicae | *Angelica* root |
| Bai Shao | Radix Paeoniae | White peony root |
| Chi Shao | Radix Paeoniae | Red peony root |
| Chuan Xiong | Rhizoma Ligustici | Sichuan lovage |
| Tao Ren | Semen Persicae | Peach seed |
| Hong Hua | Flos Carthami | Safflower flower |
| Gou Qi Zi | Fructus Lycii | *Lycium* fruit |
| Yi Mu Cao | Herba Leonuri | Motherwort herb |
| Chong Wei Zi | Semen Leonuri | Motherwort seed |

For Follicular 910, some examples of base herbal formulas may include:

Enrich 911—Builds blood and resolves blood stasis in the lower jiao.

| Enrich | | |
|---|---|---|
| Pin Yin | Latin | English Common |
| Shu Di Huang | Radix Rehmanniae | Cooked *Rehmannia* |
| Shan Yao | Rhizoma | Common yam |
| Shan Zhu Yu | Fructus Corni | Medicinal cornel |
| Fu Ling | Poria | Poria |
| Ze Xie | Rhizoma Alismatis | Oriental water |
| Mu Dan Pi | Cortex Moutan | Tree peony bark |
| Dang Gui | Radicis Angelicae | *Angelica* root |
| Bai Shao | Radix Paeoniae | White peony root |
| Chuan Xiong | Rhizoma Ligustici | Sichuan lovage |
| Gou Qi Zi | Fructus Lycii | *Lycium* fruit |
| Gui Ban | Plastrum Testudinis | Tortoise plastron |

Cool 912—Nourishes Liver blood and Kidney yin, generates fluids and strongly clears heat.

| Enrich and Cool | | |
|---|---|---|
| Pin Yin | Latin | English Common |
| Shu Di Huang | Radix Rehmanniae | Cooked *Rehmannia* |
| Shan Yao | Rhizoma | Common yam |
| Shan Zhu Yu | Fructus Corni | Medicinal cornel |
| Fu Ling | Poria | Poria |
| Ze Xie | Rhizoma Alismatis | Oriental water |
| Xuan Shen | Radix | *Scrophularia* root |
| Dang Gui | Radicis Angelicae | Angelica root |
| Bai Shao | Radix Paeoniae | White peony root |
| Sheng Di Huang | Radix Rehmanniae | *Rehmannia* root |

-continued

| Enrich and Cool | | |
| --- | --- | --- |
| Pin Yin | Latin | English Common |
| Chi Shao | Radix Paeoniae | Red peony root |
| Zhi Mu | Radix | Common |
| Tian Men Dong | Radix Asparagi | *Asparagus* tuber |
| Huang Bai | Cortex Phellodendri | Amur cork tree bark |
| Huang Qin | Radix Scuttellariae | Baikal skullcap root |
| Zhi Zi | Fructus Gardeniae | *Gardenia* fruit |
| Han Lian Cao | Herba Ecliptae | *Eclipta* herb |
| Nu Zhen Zi | Fructus Ligustri | *Ligustrum lucidum* |
| He Huan Pi | Cortex Albiziae | *Albizia* bark |
| Suan Zao Ren | Semen Zizyphi | Spiny date seed |

Regulate 913—Nourishes yin and blood to regulate liver qi.

| SI Ni San | | |
| --- | --- | --- |
| Pin Yin | Latin | English Common |
| Chai Hu | Radix Bupleuri | *Bupleurum*; Red |
| Zhi Shi | Fructus Aurantii | Immature bitter |
| Bai Shao | Radix Paeoniae | White peony root |
| Zhi Gan Cao | Radix Glycyrrhizae | Honey fried licorice |

Energize 914—Tonifies Spleen qi and drains damp.

| Liu Jun Zi Tang | | |
| --- | --- | --- |
| Pin Yin | Latin | English Common |
| Ren Shen | Radix Ginseng | Ginseng root |
| Bai Zhu | Rhizoma | White *attractylodes* |
| Fu Ling | Poria | Poria |
| Gan Cao | Radix Glycyrrhizae | Licorice root |
| Chen Pi | Pericarpium Citri | Citrus peel (orange |
| Ban Xia | Rhizoma Pinelliae | *Pinellia* tuber |

For Luteal 915, some examples of base herbal formulas may include:

Warm 916—Warms the Kidney yang and tonifies Spleen qi.

| Warm | | |
| --- | --- | --- |
| Pin Yin | Latin | English Common |
| Fu Zi | Radix Aconiti | Aconite root |
| Rou Gui | Cortex Cinnamomi | Cinnamon bark |
| Shu Di Huang | Radix Rehmanniae | Cooked *Rehmannia* |
| Shan Zhu Yu | Fructus Corni | Medicinal cornel |
| Shan Yao | Rhizoma | Common yam |
| Fu Ling | Poria | Poria |
| Ze Xie | Rhizoma Alismatis | Oriental water |
| Bai Shao | Radix Paeoniae | White peony root |
| Dang Gui | Radicis Angelicae | *Angelica* root |
| Tu Si Zi | Semen Cuscutae | Doffer seed |
| Xu Duan | Radix Dipsaci | *Dipsacus* root |
| Rou Cong Rong | Herba Cistanches | Desert-living |
| Lu Rong | Cornu Cervi | Hairy deer horn |
| Gui Zhi | Ramulus | Cinnamon twigs |
| Yin Yang Huo | Herba Epimedii | *Epimedium* herb |
| Chai Hu | Radix Bupleuri | *Bupleurum* root |
| Xiang Fu | Rhizoma Cyperi | Nut Grass Rhizome |
| He Huan Pi | Cortex Albiziae | Mimosa Tree Bark |

Lift 917—Rescues prolapsed qi and tonifies Spleen.

| Bu Zhong Yi Qi | | |
| --- | --- | --- |
| Pin Yin | Latin | English Common |
| Huang Qi | Radix Astragali | *Astragalus* root |
| Ren Shen | Radix Ginseng | Ginseng root |
| Bai Zhu | Rhizoma | White *attractylodes* |
| Zhi Gan Cao | Radix Glycyrrhizae | Honey-fried licorice |
| Dang Gui | Radicis Angelicae | *Angelica* root |
| Chen Pi | Pericarpium Citri | Cirtus peel (orange |
| Chai Hu | Radix Bupleuri | *Bupleurum*; Red |
| Sheng Ma | Rhizoma | *Cimicifuga*; skunk |

Unwind 918—Tonifies Spleen qi and Liver blood to regulate Liver qi.

| Unwind | | |
| --- | --- | --- |
| Pin Yin | Latin | English Common |
| Chai Hu | Radix Bupleuri | *Bupleurum*; Red |
| Dang Gui | Radicis Angelicae | *Angelica* root |
| Bai Shao | Radix Paeoniae | White peony root |
| Chi Shao | Radix Paeoniae | Red peony root |
| Bai Zhu | Rhizoma | White *attractylodes* |
| Fu Ling | Poria | Poria |
| Zhi Gan Cao | Radix Glycyrrhizae | Honey fried licorice |
| Huang Qin | Radix Scuttellariae | Baikal skullcap root |
| Mu Dan Pi | Cortex Moutan | Tree peony bark |
| He Huan Pi | Cortex Albiziae | *Albizia* bark |
| Jie Cao | Radix et Rhizoma | Valerian root |
| Yu Jin | Radix Curcumae | Turmeric tuber root |
| Yuan Zhi | Radix Polygalae | Siberian milkwort |
| Xiang Fu | Rhizoma Cyperi | *Cyperus* rhizome |
| Bo He | Herba Menthae | Mint |

The Conceivable Formula Worksheets (Collected Data)

FIGS. 11A-11E show various worksheets used as input for the Conceivable Formulas. This information is used in the Conceivable Software Program algorithm to interpret the collected data and to recommend actionable changes for the individual users to improve their fertility cycle.

FIG. 11A shows the Conceivable Potential Scores 1100 including Cycle Health 1105 (30), BBT 1110 (40), Profile 1115 (10) and Lifestyle 1120 (20), which adds up to the Total Score 1125 (100).

FIG. 11B shows one example of the input that the user would put in for Cycle Health Scores 1130 for each of the following categories: Length of period 1131 (20), Days Bleeding 1132 (15), blood Color 1133 (10), Clotting 1134 (10), Volume 1135 (15), Cramping 1136 (10), PMS 1137 (10) and Cervical Fluid 1138 (10).

As shown on the worksheet, the user will enter the scoring for each of the categories based on their personal information to determine their total Cycle Health Score 1139. Each of the categories has a scoring metric used to determine the score for that particular section. For the Cycle Health Scores 1130 there are many facets to cycles that affect fertility, and what a lot of women consider "normal" are actually indications of larger problems. Each of the categories has a perfect score that can vary depending on the user. Below are the categories, with the perfect score in parenthesis next to the category, with the range changes from the perfect score shown in FIG. 11B.

Length of the cycle (20)—A perfect score of 20 is a 28 day cycle. For every day above or below 28 the score drops, as shown in FIG. 11B.

Days Bleed (15)—A perfect score of 15 is 4 days. More or less days lowers the score, as shown in FIG. 11B.

Blood Color (10)—A fresh color is a perfect score of 10. As the color changes, the score goes down, as shown in FIG. 11B.

Clotting (10)—A perfect score is no clotting, receiving a score of 10. If there is clotting, the size of the clot, dime to half dollar size, lowers the score, as shown in FIG. 11B.

Blood Volume (15)—The volume soaks in a pad of 4 gets a perfect score of 15. More or less lowers the score, as shown in FIG. 11B.

Cramping (10)—No cramping gets a perfect score of 10. As more cramping occurs, the score goes down, as shown in FIG. 11B.

PMS (10)—The severity of PMS determines the score. No PMS gets a perfect score or 5 and the scores is reduced as PMS becomes more severe, as shown in FIG. 11B.

Cervical Fluid (10) has three components, copious, clear and sticky. If all three exist and are correct, each gets a score of 3 and there is a bonus point of 1 that gives it a perfect score (10), as shown in FIG. 11B.

FIG. 11C shows one example of the input that the user would put in for Basal Body Temperature ("BBT") scores 1140 for each of the following categories: Volatility 1141 (20), Average Follicular Temp 1142 (20), Average Luteal Temp 1143 (20), Follicular Length (20) 1144 and Luteal Length 1145 (20). As shown on the worksheet, the user will enter the scoring for each of the categories based on their personal information to determine their total Basal Body Temperature Score 1146. Each of the categories has a scoring metric used to determine the score for that particular section. While no one has the perfect cycle, the use of the Conceivable Software Program should be able to get the user closer. Each of the categories has a perfect score that can vary depending on the user. Below are the categories, with the perfect score in parenthesis next to the category, with the range changes from the perfect score shown in FIG. 11C.

Volatility (20)—SD=0.1 is a perfect score of 20. As SD gets larger, the points go down, as shown in FIG. 11C.

Average Follicular Phase Temp (20)—The ideal temperature for the Follicular Phase is 97.2-4, which is a perfect score of 20. As the temperature goes up or down from this number, the score is reduce, as shown in FIG. 11C.

Average Luteal Phase Temp (20)—The ideal temperature for the Luteal Phase is 98.2+ for a score of 20. As the temperature goes down, the score is reduces, as shown in FIG. 11C.

Follicular Length (20)—The ideal Follicular length is 10 days, for a score of 20. The score is reduced for longer or shorter Follicular length, as shown in FIG. 11C.

Luteal Length (20)—The ideal Luteal length is 15+ days, for a score of 20. The score is reduced for shorter Luteal lengths, as shown in FIG. 11C.

FIG. 11D shows one example of the input that the user would put in for Profile Scores 1150 for each of the following categories: Hot 1151 (15), Cold 1152 (15), Stuck 1153 (15), Pale 1154 (15), Tired 1155 (15), Energy 1156 (5), Digestion 1157 (5), Elimination 1158 (5), Sleep Quality 1159 (5) and Mood 1160 (5). As shown on the worksheet, the user will enter the scoring for each of the categories based on their personal information to determine their total Profile score 1161.

The Fertility profile gives insight into some of the underlying issues that may be affecting the user's fertility. While no one has the perfect cycle, the use of the Conceivable Software Program should be able to get the user closer. Each of the categories has a perfect score that can vary depending on the user. Below are the categories, with the perfect score in parenthesis next to the category, with the range changes from the perfect score shown in FIG. 11D.

Hot (15) might include high follicular phase basal body temperatures, scanty cervical discharge, insomnia (harder to stay asleep)—a perfect score of 15 is 0 hot. The score decreases as the hot increases, as shown in FIG. 11D.

Cold (15) might include low luteal phase basal body temperatures, cold hands and feet, frequent urination—a perfect score of 15 is 0 cold. The score decreases as the cold increases, as shown in FIG. 11D.

Stuck (15) might include PMS, erratic temperatures across the cycle, irritability—a perfect score of 15 is 0 stuck. The score decreases as the stuck increases, as shown in FIG. 11D.

Pale (15) might include scanty menstrual blood, anxiety, pale skin—a perfect score of 15 is 0 pale and score decreases as the pale increases, as shown in FIG. 11D.

Tired (15)—a perfect score of 15 is 0 for tired and decreases as the user gets tired, as shown in FIG. 11D.

Energy (5) might include fatigue or the amount of energy the user has and is ranked by the user between 1-5, 5 being high energy and the score decreasing as the energy level goes down, as shown in FIG. 11D.

Digestion (5) might include gas and bloating, which receives a max score of 5 for normal digestion and a score of 0 for any other, as shown in FIG. 11D.

Elimination (5) might include loose stool, which receives a max score of 5 for normal elimination and a score of 0 for any other, as shown in FIG. 11D.

Sleep Quality (5) receives a max score of 5 for normal sleep quality and a score of 0 for any other, as shown in FIG. 11D.

Mood (5) receives a max score of 5 for if happy and a score of 0 for any other mood, as shown in FIG. 11D.

FIG. 11E shows one example of the input that the user would put in for Lifestyle Scores 1170 for each of the following categories: Herbs 1171 (40), Sleep 1172 (30), Hydration 1173 (15) and Diet 1174 (15). As shown on the worksheet, the user will enter the scoring for each of the categories based on their personal information to determine their Lifestyle score 1175. Below are the categories, with the perfect score in parenthesis next to the category, with the range changes from the perfect score shown in FIG. 11E.

Herbs (40) the herbs need to be taken every day. To get the maximum score of 40, the user does not miss any days. As days are missed, the score decreases, as shown in FIG. 11E. Miss one day, −1, miss two days, −3, miss three days, −5, as shown in FIG. 11D.

Sleep (30)—The body needs sleep and the more sleep the better. A maximum score is achieved if the user sleeps more than eight hours (8+). As the number of sleep hours decrease, so does the score, as shown in FIG. 11D.

Hydration (15)—The body needs hydration and the more the better. A maximum score is achieved if the user 8+ eight oz. glasses of water per day. As the number of sleep drinks decrease, so does the score, as shown in FIG. 11D.

Diet (15)—The body needs a good diet. A maximum score is achieved if the diet is good, such as 8+ servings of veggies a day. As the diet decrease, so does the score, as shown in FIG. 11D.

After the user enters the data from the Conceivable Formula worksheets (Collected data) into the Conceivable Software Program, the program will calculate a Conceivable Potential score. The Conceivable Potential score is a measure on how close they are to their optimal fecundability. An ideal score is 100. The Conceivable Software Program will make suggestions on how the user can increase their fertility score so that they may move from the user's personalized fertility state toward the ideal fertility state. The optimum goal is to make the correct changes to their lifestyle to increase their chance of conception with the use of herbs.

FIGS. 12A-12D show many example recommendations the user can make for a number of conditions that may be preventing them from moving toward the ideal Fertility Profile. The examples show different conditions that may be changed including: Clotting 1201, Cramping 1202, Volume 1203, Color 1204, Ovulation 1205, Cervical Fluid 1206, PMS Severity 1207, PMS Symptoms 1208, Spotting 1209, Follicular Temperature 1210, Luteal Temperature 1211, Sleep 1212, Water 1213, Veggies 1214, Energy 1215, Stress 1216, Digestion 1217, Sleep Quality 1218, Mood 1219 and Elimination 1220.

FIGS. 13A-13B show one example of the Triggers that may be experienced by the user, including: trigger_id 1301, trigger_comparison 1302, trigger_field 1303, period 1304, trigger_name 1305, trigger_event 1306, Notes 1307 and trigger_value 1308.

FIG. 14 shows one example of a user's menstrual cycle of 28 cycle days ("CD") long, including the Trigger Event 1401, Period 1402 and the Trigger Field 1403. In this example, the Trigger Field 1403 shows what is happening on each of the 28 cycle days.

One Example of Using the Conceivable Software Program

The Conceivable Software Program includes many different settings to help or remind the user to do different things to enter important information into the software program. The software program instructs the user to input data at critical times to accurately determine the correct fertility score. This information is used to help the user alter or change their lifestyle to increase the chance of fertility. After the information is entered, the software program determines a score for the user and then may make suggestions on how the user can increase their fertility score by lifestyle changes and herbs.

Below is an example of the type of Tracking information that is input into the Conceivable Software Program. At different points during the monthly cycle, different information may be input into the Conceivable Software Program.

A) Basal Body Temperature ("BBT')
  BBT—When first logging on the user might receive a message for BBT: "First thing in the morning, before getting out of bed, take your temperature. Try recording your temperature around the same time every morning."

B) Daily Recording To The Conceivable Software Program
  Sleep—"How many hours of sleep did you get last night?: 3-8+"
  Water—"How many 8 oz. glasses of water did you drink today?: 1-8+"
  Veggies—"How many servings of veggies did you eat today?: 1-8+"
  Digestion—"What are you experiencing most?"
    Bloating
    Gas
    Nausea
    Heartburn
    Stomach ache
    It's good!
  Energy—"Rate the amount of energy you have: 1-5"
  Stress—"Rate the amount of stress you are experiencing: 1-5"

C) Herbs
  "Check your bottle for dosage, or contact your practitioner with any questions. Check Morning, Noon and Night."

D) Cycle
  Cervical Discharge—"You may be close to ovulation, do you have abundant, clear and sticky discharge?"

E) Profile
  Fertility Profile—"Your fertility profile gives us insight into some of the underlying issues that may be affecting your fertility. Let's dig in a little deeper to get a better idea of how you're feeling. Answer the questions below."
    Elimination—What do you experience most in elimination?"
      Loose Stool
      Regular/formed
      Constipated
    Sleep—How's your sleep been?"
      trouble falling asleep
      pretty good
      trouble staying asleep.
    Mood—"What mood has been the most prevalent for you?"
      Irritable/Angry
      Anxious
      Depressed
      Happy/Joy
      Worried
      N/A F) Bleeding
  The user should also keep track of bleeding, such as when there is spotting or the start of the period (bleeding cycle).

The Conceivable Software Program may also include different alarms (that can be turned on and off) to give the user reminders. For example the software program may include:
  Herb Reminder
    Morning (user may set the reminder time)
    Afternoon (user may set the reminder time)
    Evening (user may set the reminder time)
  BBT Reminder (user may set the reminder time)
  Tracking Information, such as discussed above (user may set the reminder time)

Conceivable Software Program may also provide educational information for the user to help educate them on the different items happening during the cycle. For example:
  Cycle Health—There are many facets to cycles that affect fertility, and what a lot of women consider "normal" are actually indications of larger problems. While no one has the perfect cycle, the use of the Conceivable Software Program should be able to get the user closer.
    Blood Color
    Clotting
    Blood Volume
    Cramping
    PMS
    Cervical Fluid
  Basel Body Temperature (BBT)
    BBT In The Follicular Phase
    BBT In The Luteal Phase
    Adjusting Your BBT
    Fertility Hurdles Fertility Hurdles
The Pale Hurdle
The Tired Hurdle
The Stuck Hurdle
The Hot Hurdle
The Cold Hurdle
Digestion And Elimination
Energy
Sleep
Mood
Lifestyle
Water
Veggies
Acupuncture
Pregnancy As the information is entered, the Conceivable Software Program keeps track of your Conceivable Potential (the measure of how close the user is to their personalized optimal fertility self). By keeping track of the information, the Conceivable Software Program is able to track the users Fertility Profile in real-time and suggest improvements to the user of the symptoms that constitute any Conceivable Hurdles that reflect the changes that they are making and that are working. Including the herbal formulas they are taking. The optimum goal to make the correct changes to reduce the presence of any hurdles, shown above, or any other issues, so that the user can achieve their Maximum fecundity.

Herbal Formulas for Infertility.

One key to the present invention is the ability to assess the user's health through the Conceivable Software Program and then utilize the assessment data to provide input to the user to make a measurable change in the users health. Once the user's individual input and calculations are completed with the Conceivable Software Program, Conceivable provides the best personalized diet, lifestyle coaching, and herbal mixture for the user particular conditions or hurdles.

The specifically designed personalized herbal mixture is for users dealing with infertility. The herbs are specifically formulated to address issues like irregular BBT, weak menstrual cycles, irregular ovulation, and painful periods, all of which can be key contributors to infertility.

A Customizable Software Program for Non-Fertility Issues.

In some embodiments, the Conceivable Software Program may be modified or customized for non-fertility wellness. For example, the software program may be a customized, actionable lifestyle modification program for the purpose of improving medical outlook or prognosis, or maintaining wellness, not necessarily improving fertility. The software program could be modified to deal with other issues using herbs, such as diabetes, weight loss, lung dysfunction, kidney dysfunction, cardiovascular dysfunction, weight gain or other dysfunctions, etc. Below is a non-fertility example of the software program.

Non-Fertility Example of Using the Software Program

The Conceivable Software Program includes many different settings to help or remind the user to do different things to enter important information into the software program. While the normal Conceivable Software Program is used for fertility, the software program may also be modified or customized to help the user alter or change their lifestyle to improving medical outlook or prognosis, or maintaining wellness. For example, the modified or customized Software Program may decrease an individual's risk of developing, for example, Type II Diabetes, lung dysfunction, kidney dysfunction, cardiovascular dysfunction, weight gain or other dysfunctions. One objective of the Software Program is to improve the health of the user through the use of information and herbs. The Software Program may also be tailored to a certain group of individuals, e.g., a group of individuals who are at an elevated risk for Type II Diabetes or who have an elevated risk of high blood pressure or cardiovascular dysfunction.

After the information is entered, the software program may make suggestions on how the user can make actionable lifestyle modifications and select/recommend herbs to make the changes. Below is an example of information that may be input into the Software Program that might be used to help a user with other lifestyle issues.

A) Daily Recording To The Software Program
    Sleep—"How many hours of sleep did you get last night?: 3-8+"
    Water—"How many 8 oz. glasses of water did you drink today?: 1-8+"
    Veggies—"How many servings of veggies did you eat today?: 1-8+"
    Digestion—"What are you experiencing most?"
        Bloating
        Gas
        Nausea
        Heartburn
        Stomach ache
        It's good!
    Energy—"Rate the amount of energy you have: 1-5"
    Stress—"Rate the amount of stress you are experiencing: 1-5"
B) Herbs
    "Check your bottle for dosage, or contact your practitioner with any questions. Check Morning, Noon and Night."
C) Profile
    Elimination—What do you experience most in elimination?"
        Loose Stool
        Regular/formed
        Constipated
    Sleep—How's your sleep been?"
        trouble falling asleep
        pretty good
        trouble staying asleep.
    Mood—"What mood has been the most prevalent for you?"
        Irritable/Angry
        Anxious
        Depressed
        Happy/Joy
        Worried
        N/A
    Weight gain/loss?
        What are you eating
        How much are you eating
        Weight fluctuation The Software Program may also include different alarms (that can be turned on and off) to give the user reminders. For example the software program may include:
    Herb Reminder
        Morning (user may set the reminder time)
        Afternoon (user may set the reminder time)
        Evening (user may set the reminder time)
        Tracking Information, such as discussed above (user may set the reminder time)

The Software Program may also provide educational information for the user to help educate them on different medical problems that the Software Program may think is happening to them from the information they have input into the program. For example, through the information input, the Software Program provide educational information on:

Diabetes
Lung Dysfunction
Kidney Dysfunction
Cardiovascular Dysfunction
High Blood Pressure
Weight Gain
Other Dysfunctions From The Information Entered It is believed that the construction, operation and advantages of this invention will be apparent to those skilled in the art. It is to be understood that the present disclosure is illustrative only and that changes, variations, substitutions, modifications and equivalents will be readily apparent to one skilled in the art and that such may be made without departing from the spirit of the invention.

It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claims set forth herebelow not be construed as being order-specific unless such order specificity is expressly stated in the claim.

Various embodiments of the invention have been presented in a range format. It should be understood that the description in range format is merely for convenience and brevity and should not be construed as an inflexible limitation on the scope of the invention. The ranges disclosed herein encompass any and all overlap, sub-ranges, and combinations thereof, as well as individual numerical values within that range. Language such as "up to," "at least," "greater than," "less than," "between," and the like includes the number recited. Numbers proceeded by a term such as "about" or "approximately" include the recited numbers.

The invention claimed is:

1. A method of increasing chances of conception, comprising:
    providing a portable electronic device having a processor and a memory that executes a mobile application that is configured to:
    receive, by the portable electronic device, data about a fertility state of a user;
    assess personalized fertility state of the user based on the received data of the fertility state of the user;
    wherein assessing the user's personalized fertility state includes collecting data on menstrual parameters, lifestyle factors, and Basal body temperatures ("BBT's");
    assigning the user, one or more hurdles of one or more symptoms that represents underlying fertility issues of the user;
    determine a deviation between the user's personalized fertility state and an ideal fertility state;
    algorithmically identify the user's underlying fertility issues based on the determined deviation from the ideal fertility state;
    store, in the mobile application, a plurality of herbal formulas targeted at moving the user's personalized fertility state toward the ideal fertility state;
    compare, by the mobile application, the underlying fertility issues with the stored herbal formulas;
    select, by the mobile application, based on the underlying fertility issues and a phase of a menstrual cycle of the user, a personalized herbal formula recommendations for the user to take to move the user's personalized fertility state toward the ideal fertility state;
    wherein after the one of more hurdles are assigned, the personalized herbal formula recommendations for the user are recommended based on the underlying fertility issues and phases of the menstrual cycle of the user; and
    display the personalized herbal formula recommendations for the user.

2. The method of claim 1, wherein said collecting data comprises collecting data on high, low, or erratic BBT's across the menstrual cycle of the user, menstrual clotting, menstrual pain, insufficient menstrual flow, hemorrhagic menstrual flow, insufficient cervical discharge, irregular ovulation, symptoms associated with premenstrual syndrome (PMS) including one or more of bloating, irritability, headaches, breast tenderness, and cramping, and spotting.

3. The method of claim 1, wherein said collecting data further comprises identifying subclinical factors and their causes that affect the user's personalized fertility state and the user's ability to conceive.

4. The method of claim 3, wherein the one or more hurdles and their main associated symptoms are selected from the group consisting of:
    a) hot—high follicular phase basal body temperatures, scanty cervical discharge, insomnia (harder to stay asleep);
    b) cold—low luteal phase basal body temperatures, cold hands and feet, frequent urination;
    c) stuck—premenstrual syndrome (PMS), erratic temperatures across the menstrual cycle of the user, irritability;
    d) pale—scanty menstrual blood, anxiety, pale skin; and
    e) tired—fatigue, gas and bloating, loose stools, weight gain or retention.

5. The method of claim 4, wherein a goal for the phases of the menstrual cycle to support fertility wellness are selected from the group consisting of:
    a) bleeding—Remove old, clotty, or stale uterine lining through menstrual bleeding, decrease menstrual pain, improve uterine blood flow, support production of a healthy amount of uterine bleeding;
    b) follicular—Regulate BBT, build a healthy and sufficient new uterine lining, regulate ovulation, promote a healthy environment for follicular development and egg maturation; and
    c) luteal—Regulate BBT, enhance progesterone function, stabilize uterine lining, maintain pregnancy.

6. The method of claim 5, wherein the personalized herbal formula recommendations to address the underlying fertility issues are provided once step of selecting the goal is completed.

7. The method of claim 1, further comprising providing the user with one or more of fertility acupuncture care, other complementary, alternative, holistic, or allopathic fertility care, wellness providers, clinics specifically designed according to the underlying fertility issues of the user.

* * * * *